United States Patent [19]
Ameer et al.

[11] Patent Number: 6,099,730
[45] Date of Patent: Aug. 8, 2000

[54] APPARATUS FOR TREATING WHOLE BLOOD COMPRISING CONCENTRIC CYLINDERS DEFINING AN ANNULUS THEREBETWEEN

[75] Inventors: Guillermo Ameer, Plano, Tex.; Rober S. Langer, Jr., Newton, Mass.; Maria Rupnick, Malden, Mass.; Hidde L. Ploegh, Brookline, Mass.; Eric Grovender, Allston, Mass.

[73] Assignee: Massachusetts Institute of Technology, Cambridge, Mass.

[21] Appl. No.: 09/191,175

[22] Filed: Nov. 13, 1998

Related U.S. Application Data

[60] Provisional application No. 60/066,017, Nov. 14, 1997, and provisional application No. 60/066,018, Nov. 14, 1997.

[51] Int. Cl.$^7$ .............................. B01D 33/00; B01D 63/00
[52] U.S. Cl. ................................ 210/321.67; 210/321.68; 210/650; 210/651; 435/297.3
[58] Field of Search ..................... 210/650, 651, 210/782, 321.67, 321.68; 435/297.1, 297.2, 297.3; 436/528, 531, 532

[56] References Cited

U.S. PATENT DOCUMENTS

| | | |
|---|---|---|
| 3,705,100 | 12/1972 | Blatt et al. . |
| 3,750,885 | 8/1973 | Fournier .................................. 210/108 |
| 3,888,250 | 6/1975 | Hill ........................................ 210/494 |
| 4,373,023 | 2/1983 | Langer et al. ............................... 435/2 |
| 4,609,461 | 9/1986 | Takata et al. ......................... 210/195.2 |
| 4,713,176 | 12/1987 | Schoendorfer et al. ................ 210/645 |
| 4,790,942 | 12/1988 | Schmidt et al. ......................... 210/650 |
| 4,808,307 | 2/1989 | Fischel et al. ...................... 210/321.68 |
| 4,846,786 | 7/1989 | Freed et al. .................................. 604/4 |
| 5,194,157 | 3/1993 | Ghezzi et al. ........................... 210/646 |
| 5,240,614 | 8/1993 | Ofsthun et al. .......................... 210/645 |
| 5,464,534 | 11/1995 | Fischel ................................ 210/321.68 |
| 5,480,552 | 1/1996 | Soltys et al. ............................. 210/645 |
| 5,527,467 | 6/1996 | Ofsthun et al. .......................... 210/645 |
| 5,762,791 | 6/1998 | Deniega et al. .................... 210/321.67 |
| 5,773,384 | 6/1998 | Davankov, et al. ..................... 502/402 |

FOREIGN PATENT DOCUMENTS

| | | |
|---|---|---|
| 0 231 623 | 8/1987 | European Pat. Off. . |
| 0 310 205 | 4/1989 | European Pat. Off. . |
| 0 112 152 | 1/1991 | European Pat. Off. . |
| 0 464 707 | 1/1992 | European Pat. Off. . |
| 0 194 271 | 3/1992 | European Pat. Off. . |
| 0 819 439 | 1/1998 | European Pat. Off. . |
| 3 406 562 | 8/1985 | Germany . |
| 85/04112 | 9/1985 | WIPO . |
| 88/01193 | 2/1988 | WIPO . |
| 90/00922 | 2/1990 | WIPO . |
| 97/32653 | 9/1997 | WIPO . |
| 97/48483 | 12/1997 | WIPO . |

OTHER PUBLICATIONS

Stuart, "Taylor–Vortex Flow: A Dynamical System," *SIAM Review* 28(3):315–342, Sep. 1986.

Beaudoin, et al., "High Efficiency Plasmapheresis Using Rotating Membrane Device," *Life Support Systems* 5:273–278, 1987.

(List continued on next page.)

*Primary Examiner*—John Kim
*Attorney, Agent, or Firm*—Choate, Hall & Stewart

[57] ABSTRACT

Apparatus for removing substances from blood is disclosed. The apparatus includes concentric cylinders defining an annulus therebetween with the inner cylinder adapted for rotation with respect to the outer cylinder. At least one of the cylinders includes a porous membrane covered portion forming a compartment containing an immobilized active species. The active species is adapted to break down or remove the substance. Plasma in blood flowing in the annulus passes through the porous membrane and interacts with the active species either by reaction or binding. Red and white blood cells do not pass through the membrane. In this way, a substance is removed from plasma without exposing blood cells to the active species.

24 Claims, 17 Drawing Sheets

OTHER PUBLICATIONS

Fischel, et al., "Couette Membrane Filtration with Constant Shear Stress," *Trans. Am. Soc. Artif. Intern. Organs* 34:375–385, 1988.

Jaffrin, "Innovative Processes for Membrane Plasma Separation," *J. Membrane Sci.* 44:115–129, 1989.

Gejyo, et al., "A New Therapeutic Approach to Dialysis Amyloidosis: Intensive Removal of beta2–Microglobulin with Adsorbent Column," *Artificial Organs* 17(4):240–243, 1993.

Schlebusch, et al., "Production of a Single–Chain Fragment of the Murine Anti–Idiotypic Antibody ACA125 as Phage––Displayed and Soluble Antibody by Recombinant Phage Antibody Technique," *Hybridoma* 16(1):47–52, 1997.

Furuyoshi, et al., "New Adsorption Column (Lixelle) to Eliminate beta2–Microglobulin for Direct Hemoperfusion," *Therapeutic Apheresis* 2(1):13–17, 1998.

Slieker, et al., "Differentiation Method–Dependent Expression of Leptin in Adipocyte Cell Lines," *Biochem. & Biophys. Res. Comm.* 251:225–229, 1998.

APPARATUS FOR TREATING WHOLE BLOOD COMPRISING CONCENTRIC CYLINDERS DEFINING AN ANNULUS THEREBETWEEN

This application claims benefit and priority of U.S. Provisional Application Nos. 60/066,017 and 60/066,018, both filed Nov. 14, 1997, both of which are incorporated by reference herein.

This invention was made with government support under Grant Number NIH-2R01-GM25810 awarded by the National Institutes of Health. The government has certain rights in the invention.

BACKGROUND OF THE INVENTION

This invention relates to apparatus and method for removing substances such as drugs and toxins from whole blood.

The incidence of end-stage renal disease (ESRD) in the United States exceeds 200 per million population and continues to rise by approximately 8% per year, largely with the inclusion of elderly hypertensive and/or diabetic patients (see, for example, "Morbidity and Mortality of Dialysis," NIH Consensus Development Conference Statement, Nov. 1–3, 1993, 11:1–33). The treatment of choice for ESRD is kidney transplant. However, the limited number of donor organs, presence of qualifying co-morbidities, and low transplant rate for the elderly, ensures that hemodialysis will remain the primary method of renal replacement therapy in the foreseeable future. By the turn of the century, nearly 390,000 patients are expected to be enrolled in dialysis programs.

It is often necessary or desirable to remove substances from blood without damaging the cells contained within whole blood. An example is the desirability of removing the anticoagulant heparin from blood before the blood is returned to a dialysis patient. A well known enzyme, heparinase, reacts with heparin causing it to break down. Unfortunately, heparinase immobilized on solid supports is unsuitable for use with prior art bioreactors to remove heparin from blood, because the solid supports cause hemolysis in whole blood. A goal has been to design a bioreactor which would allow the clinical use of enzymes such as heparinase in a safe and efficient manner with whole blood. Conventional membrane reactors (hollow fibers) have the disadvantage of reduced mass transfer to a reactive membrane and therefore surface area of contact has to be maximized often resulting in infeasible devices. Fluidized beds of, for example, agarose beads result in good mass transfer but the fluid dynamics of the particles in blood can lead to hemolysis of the red cells and packing of the beads will occur at high flow rates.

Another substance which it is highly desirable to remove from the blood of dialysis patients is $\beta_2$-microglobulin, which has been implicated in dialysis related amyloidosis (DRA). DRA is a severely debilitating, potentially life-threatening, and inevitable consequence of long-term hemodialysis. It is characterized by amyloid deposits preferentially in osteoarticular locations. The clinical sequela includes chronic pain, carpal tunnel syndrome, joint deformities, destructive arthropathy, cystic bone lesions, fractures, and spondylarthropathy. The incidence and severity of DRA increases with the length of dialysis therapy, reaching 70% after 10 years and 100% after 20 years. Further information about DRA can be found in Drueke, et al, "Dialysis-associated amyloidosis," *Advan. Renal Replac. Therapy* (1995) 2:24–39, and Schaeffer et al, "Pathogenetic and diagnostic aspects of dialysis-related amyloidosis," *Nephrol. Dial. Transplant* (1995) 10(Suppl 3):4–8. DRA is the most incapacitating consequence of long-term dialysis and remains inescapable.

In the absence of established methods to treat or avoid DRA, interventions are limited to merely symptomatic relief. Patients are typically on chronic pain management with variable efficacy. Low-dose steroids relieve some of the symptoms but often have intolerable side-effects. Numerous orthopedic procedures are the rule, including carpal tunnel surgery, arthroscopic synovectomy, bursectomy, cyst curettage and filling, tendon sheath and ligament resections, and others. For advanced destructive arthropathy, prosthetic replacements of weight-bearing joints, such as the hips, are commonly necessary. In patients with destructive spondylarthropathy associated with spinal cord or nerve-root compression, orthopedic consolidation may constitute a life-saving procedure. Conservative and approximate estimates of the cost to treat the complications of DRA exceed $500 million/year.

Although the mechanisms of DRA development are under investigation, it is certain that retention of $\beta_2$M, the precursor molecule of the amyloid fibrils, is an absolute prerequisite. $\beta_2$M is a non-polymorphic single chain polypeptide (11,800 Mw) that is continually shed from cell membranes. It is a noncovalently-bound subunit of the class I Major Histocompatibility Complex. It accumulates in renal failure primarily due to diminished excretion; it has been estimated that normal kidneys remove 150 mg of $\beta_2$M per day. Typical $\beta_2$M levels in normal adults are in the range of about 1–3 mg/l blood, while renal failure levels may reach or exceed 60 mg/l blood. Chronically elevated levels of $\beta_2$M must be present for DRA to occur. This causal role is further supported by demonstrations that measures effective at reducing the supply of $\beta_2$M can slow or halt disease progression and improve symptoms. These findings strongly support the development of a system able to re-establish and maintain normal levels of $\beta_2$M with the efficiency currently only achievable with a normally functioning kidney.

Conventional hemodialysis systems, which consist of a regenerated cellulosic membrane (cuprophane), do not remove $\beta_2$M. Although inexpensive, this membrane is impermeable to proteins, such as $\beta_2$M, resulting in a progressive accumulation of this protein. Therefore, research efforts have focused on modifying the dialysis technique to lower circulating $\beta_2$M levels, in the hope of favorably impacting the occurrence rate and course of this disease.

The use of highly permeable, synthetic dialysis membranes, such as polyacrylonitrile (AN69) and polysulfone (F60) have been shown to lower levels of $\beta_2$M, especially when used in conjunction with hemofiltration or hemodiafiltration. Although substantial reductions can be attained, $\beta_2$M removal is still incomplete and accumulation of the remaining protein continues to contribute to the pathophysiology of DRA. An additional concern with these systems is the indiscriminate removal of other middle weight molecules, such as hormones and growth factors. Given the performance limitations, these dialyzers are prohibitively expensive for use in a government regulated, capitated system, such as hemodialysis.

Hemoperfusion methods involving extracorporeal adsorption columns have also been used in conjunction with synthetic membrane hemodialysers to remove $\beta_2$M. The most developed of these is the BM-01 column containing a hexadecyl alkyl compound which has recently been tested in small groups of patients. Although superior to high-flux hemodialysers alone, protein accumulation still occurs, making the expense of this combination approach impractical. This column also requires a large priming volume, which may complicate the dialysis management of cardiovascularly tenuous patients, particularly since adsorption columns tend to have a high pressure drop along the length of the column. Further, this treatment has been found to induce hypotension, a reduction in hematocrit and platelet count, and the loss of beneficial plasma proteins (mainly lysozyme). Other adsorbents that have been studied in vitro include collagen, gelatin, and various ligands. However, non-specific binding remains a concern with these approaches as none of them is geared specifically toward reduction of $\beta_2 M$ level.

Immunoadsorption approaches are attractive for their superior specificity and affinity as was demonstrated with the application of high-performance immunoaffinity chromatography to the removal of $\beta_2 M$. Unfortunately, this system is not compatible with whole blood and requires plasma separation by filtration or centrifugation before the treatment can be applied. This is not a reasonable procedure to impose on patients already debilitated by extensive chronic interventions. An alternative immunoadsorption method is the immunoaffinity column in which antibodies are immobilized onto insoluble supports. This system is also unusable with whole blood. Furthermore, the flow velocity through packed columns is limited, resulting in a relatively slow removal process. The development of hemocompatible immunoadsorbents from conventional hemodialyzers has also been proposed. Although a bifunctional device has obvious appeal, the design limitations of this technology make it inadequate for this application. The dialyzers offer a finite, and relatively small, surface area for antibody immobilization, which is most suited for removing circulating compounds present in low concentrations. This would not be sufficient to counterbalance the 1,400–2,000 mg of $\beta_2 M$ generated weekly. In addition, compared to traditional particulate matrices, antibody binding to cuprophan-based dialyzers is less stable. Therefore, a large amount of ligand is required to achieve satisfactory immobilization. This also presents concerns of antibody shedding into the circulation, deteriorating binding capacity of the system, and a potential for unwanted immunological side effects. The modified dialyzers also have decreased clearance values and increased ultrafiltration coefficients. The performance limitations and cost of these systems have remained substantial obstacles to their establishment as common clinical modalities.

Pharmacological interventions are also being explored. Low molecular weight anionic sulphonate and sulphate compounds designed to interfere with amyloid-basement membrane interactions show promise in the animal model of familial amyloidosis, although the relevance to DRA has not been investigated. In addition, aminoguanidine, which prevents the glycation of $\beta_2 M$ thought important in amyloidogenesis, is also being considered.

There is currently no renal replacement strategy that can achieve the same efficiency of $\beta_2 M$ removal as a normally functioning kidney. However, the approaches attempted thus far have provided invaluable information regarding the clinical benefits of even a partial reduction in protein load. The favorable impact on the onset and course of DRA supports the development of a system able to re-establish and maintain normal levels of $\beta_2 M$.

It is an object of the present invention to provide a bioreactor capable of removing heparin, $\beta_2 M$, or other substances from plasma with minimal or no damage to blood cells. This and other objects are achieved by the apparatus and methods described and claimed hereinbelow.

SUMMARY OF THE INVENTION

The present invention utilizes the principle of simultaneous separation and reaction within the same device to achieve a high efficiency detoxification or purification process without compromising delicate components of the feed such as the blood cells in whole blood. The apparatus of the invention achieves plasma separation and the treatment of whole blood continuously without concentrating the cells, which could lead to hemolysis and clotting.

In one aspect of the invention, an apparatus for removing unwanted substances from blood includes concentric outer and inner cylinders defining an annulus therebetween. The inner cylinder is adapted for rotation with respect to the outer cylinder. At least one of an inner surface of the outer cylinder or an outer surface of the inner cylinder includes a porous membrane covered portion forming a compartment containing an immobilized species, the species adapted to remove the unwanted substance. An inlet is provided for introducing whole blood into the annulus for flow along the cylinders. An outlet port is provided for discharging the blood and the porous membrane allows plasma within the blood to interact with the immobilized species. The immobilized species may comprise, for example, antibodies, antibody fragments, catalytic antibodies, enzymes, peptides, proteins, or living cells.

In one embodiment, the inner surface of the outer cylinder, and/or the outer surface of the inner cylinder, include a recess covered by a mesh to exclude the immobilized species, the recess acting as a collection chamber for plasma after interaction with the immobilized species. This embodiment may further include a pump for circulating plasma from the recess back into the annulus.

According to the invention, rotation of the inner cylinder above a critical angular velocity generates Taylor vortices in the annulus, the vortices creating oscillatory pressure gradients within the annulus. These pressure gradients cause periodic undulations in the unsupported porous membrane, resulting in circumferential flow in the compartment containing the immobilized species which increases the activity of the immobilized species. In a preferred embodiment, the inner cylinder is caused to rotate via magnetic coupling to an external electric motor. A suitable rotation rate is 1200 r.p.m.

In a preferred embodiment, the active species is immobilized on beads, which may comprise, for example, agarose, cellulose, or protein A. These beads may be fluidized by the undulations of the porous membrane, increasing the activity of the immobilized species. Alternatively, the active species may be organized into micelles.

In one such embodiment, the substance to be removed is heparin and the immobilized species is heparinase. In another embodiment, the unwanted substance is $\beta_2 M$-microglobulin and the immobilized species comprises antibody fragments. An apparatus for the removal of $\beta_2 M$-microglobulin may be adapted to remove as much as 0.2 g of $\beta_2$-microglobulin in a three-hour treatment, or preferably as much as 0.5 g of $\beta_2$-microglobulin in a two-hour treatment. Active volumes may be low, for example, 350 ml, 200 ml, or even 50 ml. Transmembrane flow rates in the reactor may be as high as 50 ml/min, 100 ml/min, or even 200 ml/min.

In yet another embodiment of the invention the apparatus is used for efficient and continuous plasmapheresis and no active immobilized species is required.

In a related aspect, the invention includes methods of collecting platelets from whole blood. A bioreactor similar to the one described above is provided, the bioreactor having at least two membranes to define three reaction chambers. The first membrane is adapted to pass platelets and plasma, but not larger blood cells, and the second membrane is adapted to pass only plasma. Platelets can then be continuously removed from the center chamber, while the blood cells in the main reactor chamber and the plasma in the outermost chamber are remixed and returned to the patient.

In another aspect, the invention includes methods of removing substances from whole blood. The methods are characterized by continuous isolation and reintroduction of plasma into a whole blood flow, wherein the plasma is treated to remove substances while isolated from the blood cells. In one embodiment of this aspect of the invention, a bioreactor similar to that described above may be used. The substances to be removed may be unwanted toxins, or desired substances which are collected for later use. For example, the invention may be used to collect a desired species from a transgenic animal which has been engineered to secrete that species in its blood, or the invention may be used for platelet collection.

It will be appreciated by those skilled in the art that the novel bioreactor design disclosed herein may also have utility for treatment of nonbiological slurries and mixtures. The reactor of the invention may be used for a variety of applications wherein it is desired to continuously separate a slurry or mixture, treat one component thereof, and recombine the components. This may be desirable either when the solid component is fragile or reactive, as with whole blood, or when the active species is subject to damage from the solid phase, as in certain catalysis systems.

As the terms are used herein, priming volume is considered to be the volume of the reactor occupied by red blood cells, e.g., the volume of the annular region of the reactor described above. The volume of the portion of the reactor in which the active species is contained is termed the active volume, and the total of the two represents the reactor volume.

BRIEF DESCRIPTION OF THE DRAWING

FIG. 1a is a magnified portion of FIG. 1 illustrating Taylor vortices.

DESCRIPTION OF THE PREFERRED EMBODIMENT

Figure 1:
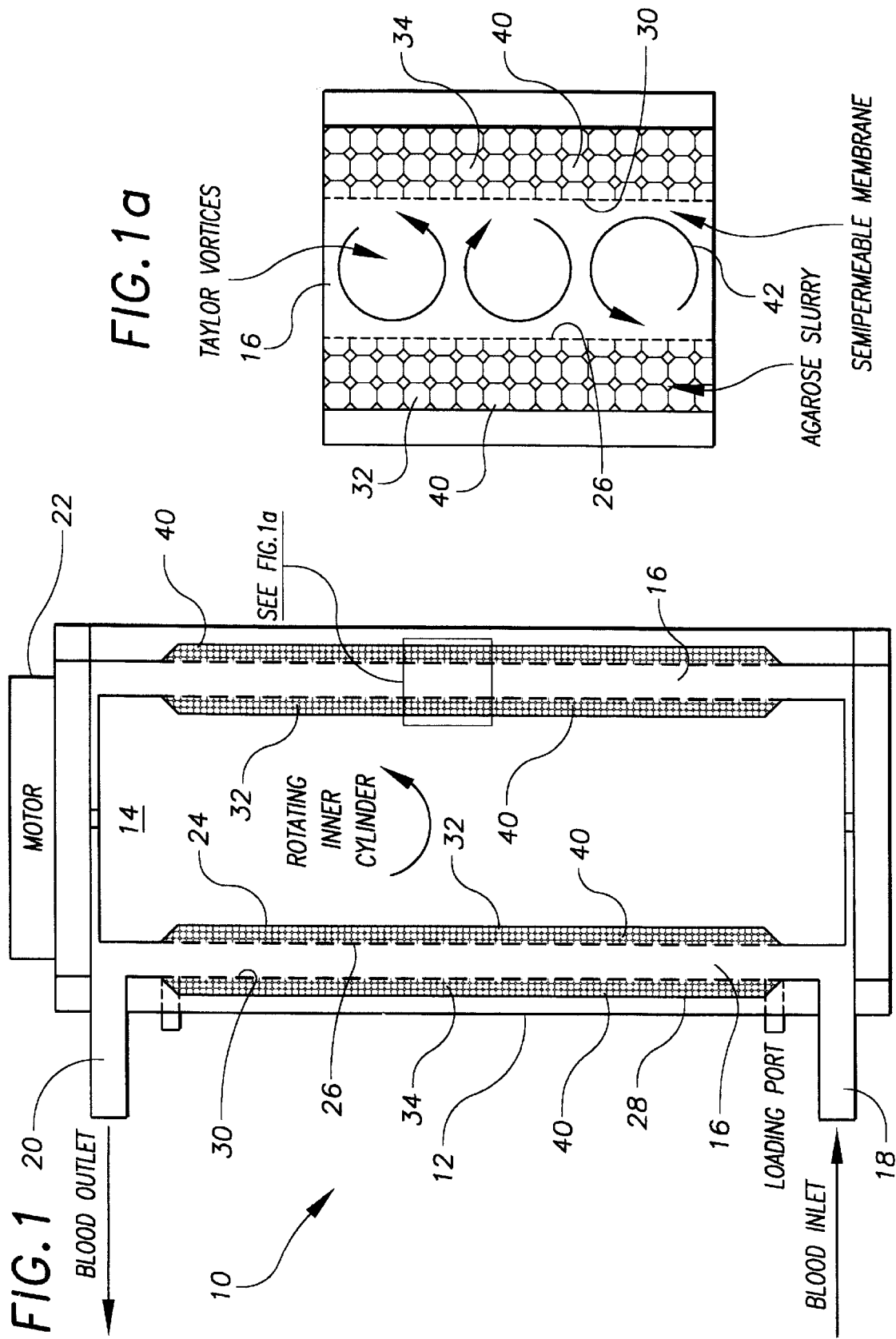
FIG. 1 is a cross sectional view of a schematic illustration of the vortex flow plasmapheretic reactor of the invention.

With reference to FIGS. 1 and 1a, a vortex flow plasmapheretic reactor 10 of the invention includes an outer cylinder 12 and a concentrically mounted inner cylinder 14. The concentrically mounted cylinders 12 and 14 define an annular chamber 16. A blood inlet 18 allows blood to flow into and along the annular chamber 16 and is discharged through a blood outlet 20.

The inner cylinder 14 is mounted for rotation within the outer cylinder 12. It is preferred that the inner cylinder 14 rotate by magnetic coupling with an external motor 22. That is, the motor 22 will contain magnets (not shown) which couple to magnets (not shown) on the top portion of the rotating inner cylinder 14. A preferred rotation rate for the inner cylinder 14 is about 1200 r.p.m.

In this embodiment, the inner cylinder 14 includes a recess 24 which may be formed by grooves covered by a porous membrane 26. Similarly, the outer, fixed cylinder 12 includes a recess 28 covered by a porous membrane 30. It is preferred that the outer and inner cylinders 12 and 14 be made of polycarbonate which is compatible with blood. It is also preferred that the porous membranes 26 and 30 be flexible polycarbonate or polyestercyclopore membranes having pore sizes in the range of 0.2–3 $\mu$m.

The recess 24 in the inner rotating cylinder 14 covered by the porous membrane 26 creates a compartment 32 which contains an active immobilized species. Similarly, the recess 28 in the outer cylinder 12 covered by the porous membrane 30 creates a compartment 34 also for containing an active immobilized species. As an example, an active species such as heparinase may be immobilized on agarose beads 40 contained within the compartments 32 and 34. As will be appreciated by those skilled in the art, an active species such as heparinase may be immobilized on agarose by first activating the agarose surface. The desired active enzyme or protein is then added. After a suitable period of time, the agarose beads containing the active species are thoroughly washed. While this specification uses heparinase as an example of an active species, it is to be understood that the invention is not limited to this enzyme. The invention comprehends the use of any active species which can interact chemically or physically with a component in blood. In particular, it is noted that the compartments 32 and 34 may include living cells for interacting with components in blood thereby allowing the reactor to act, for example, as an artificial liver. In another example, the compartments may include antibodies or antibody fragments for removal of specific proteins and compounds such as $\beta_2$M. The active species may be immobilized by being bound to a solid support, or by containment within an ultrafiltration membrane. In the latter approach, it may be advantageous for the active species to be organized into micelles, for example by incorporation of a hydrophobic group into the species. In this embodiment, the active species should organize itself into micelles with the hydrophobic component at the center and the active region at the surface of the micelle.

According to the invention, the porous membranes 26 and 30 have pores selected to prevent the passage of blood components such as red and white blood cells but which allow plasma to pass through.

When the inner cylinder 14 rotates with respect to the fixed outer cylinder 12 at a speed above a critical rotation rate, Taylor vortices 42 (FIG. 1a) are generated in the annulus 16. These vortices 42 aid in the flow of plasma into the compartments 32 and 34 so that the plasma can interact with an active species immobilized on the beads 40. It is believed that the Taylor vortices also generate oscillating pressure gradients within the annulus 16 and these pressure gradient cause periodic undulations in the flexible porous membranes 26 and 30. The undulations in a circumferential direction result in circumferential flow in the compartments 32 and 34 containing the immobilized active species. The periodic undulations of the porous membranes are similar to peristalsis and are promulgated or transferred into the fluid in the active compartments. The Taylor vortices and induced circumferential flow create fluidization of the agarose immobilized species which minimizes mass transfer limitations in the compartments 32 and 34. The presence of Taylor vortices can be predicted by the value of a characteristic Taylor number, which is a function of system dimensions, cylinder rotation rate, and fluid properties.

In this example, heparin in the plasma portion of whole blood interacts with the immobilized heparinase and is broken down so that blood exiting through the blood outlet 20 will have substantially reduced levels of heparin. The fluidization of the immobilized species retards plasma clotting in the apparatus 10 and improves mass transfer rates in the reactor.

The periodic undulations of the porous membranes which create circumferential flow in the active compartments also minimize concentration polarization at the membrane surface, thereby allowing better performance of the plasma separation process, resulting in longer device operation times at higher filtration fluxes. Experiments in sheep have been run for as long as 5 hours with filtration fluxes of 50 ml plasma per minute. Other mechanisms which produce the membrane undulations (e.g., parametric pumping, membrane vibration) will achieve a similar result of enhancing mass transfer into the active volume and minimization of concentration polarization at the membrane.

Figure 2:
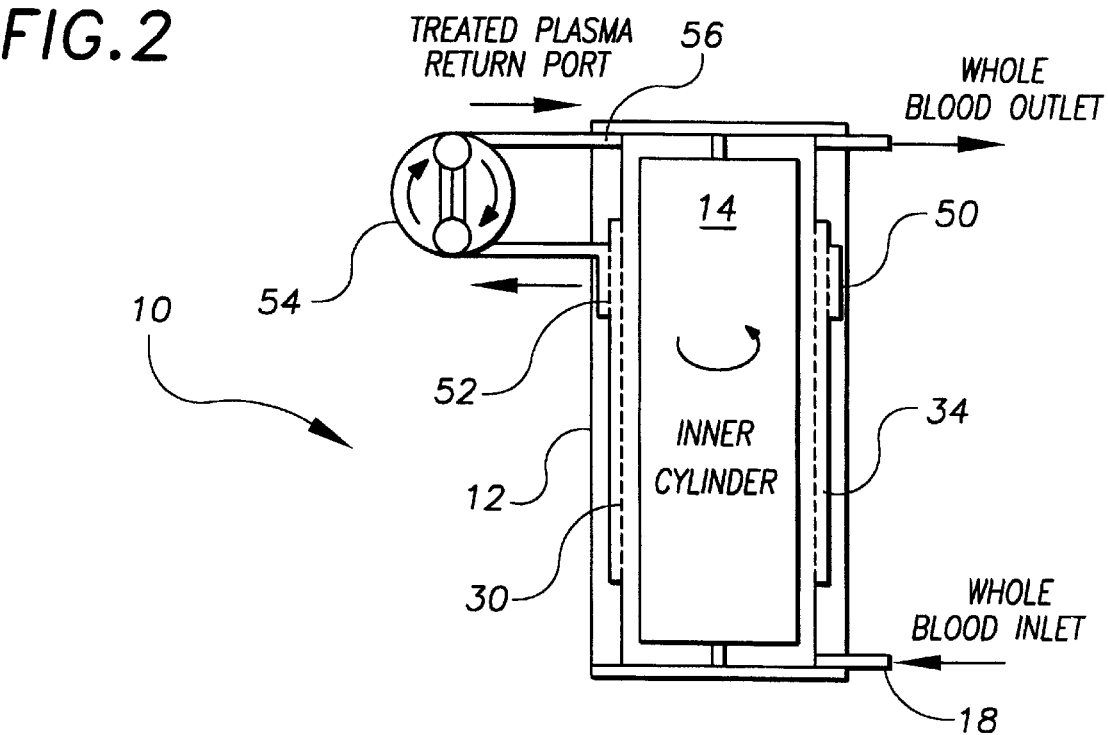
FIG. 2 is a cross sectional view of a bioreactor of the invention including a plasma pump.

With reference now to FIG. 2, an embodiment is shown with an additional recess 50 covered by a polyester mesh 52. The recess 50 will collect plasma while the polyester mesh 52 will prevent any of the immobilized active species from entering the recess 50. A plasma pump 54 transports plasma from the recess 50 and returns it at a return port 56. It is important that the treated plasma be returned directly into the device 10 either close to the whole blood outlet port (preferably) or close to the whole blood inlet port. Such a configuration eliminates concentration of cells which would precipitate clogging of the porous membrane 30. It is an added benefit that the return of the treated fluid near the whole blood inlet is able to dilute the feed thereby decreasing the hematocrit only within the device and not the patient. A lowered hematocrit in the apparatus will allow higher filtration fluxes. As in the embodiment of FIG. 1, the membrane 30 is located on the outer cylinder and is supported only at the top and bottom. The membrane is thus able to induce circumferential flow in the active compartment 34 though periodic undulations that arise from the fluid dynamics created by the rapid rotation of the inner cylinder.

Figure 3:
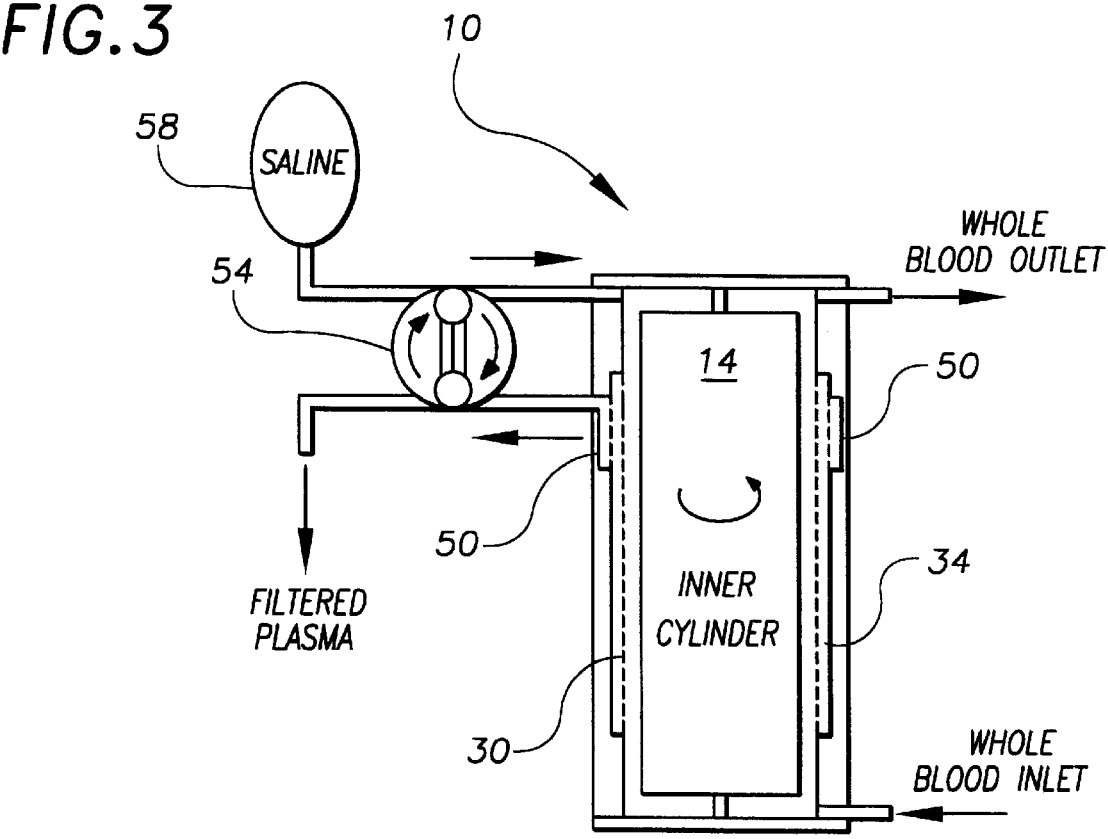
FIG. 3 is a cross sectional view of an embodiment of the invention including a double pump head for plasmapheresis.

Another embodiment of the invention is shown in FIG. 3. In this embodiment, there is no active species immobilized in the chamber 34. Rather, untreated plasma is withdrawn from the recess 50 and discharged. The pump 54 is double pump head and introduces saline from a saline reservoir 58 back into the device 10. The design of FIG. 3 ensures constant fluid balance within the device, minimizing concentration of cells due to the filtration process and preventing premature clogging of the membrane.

Figure 4:
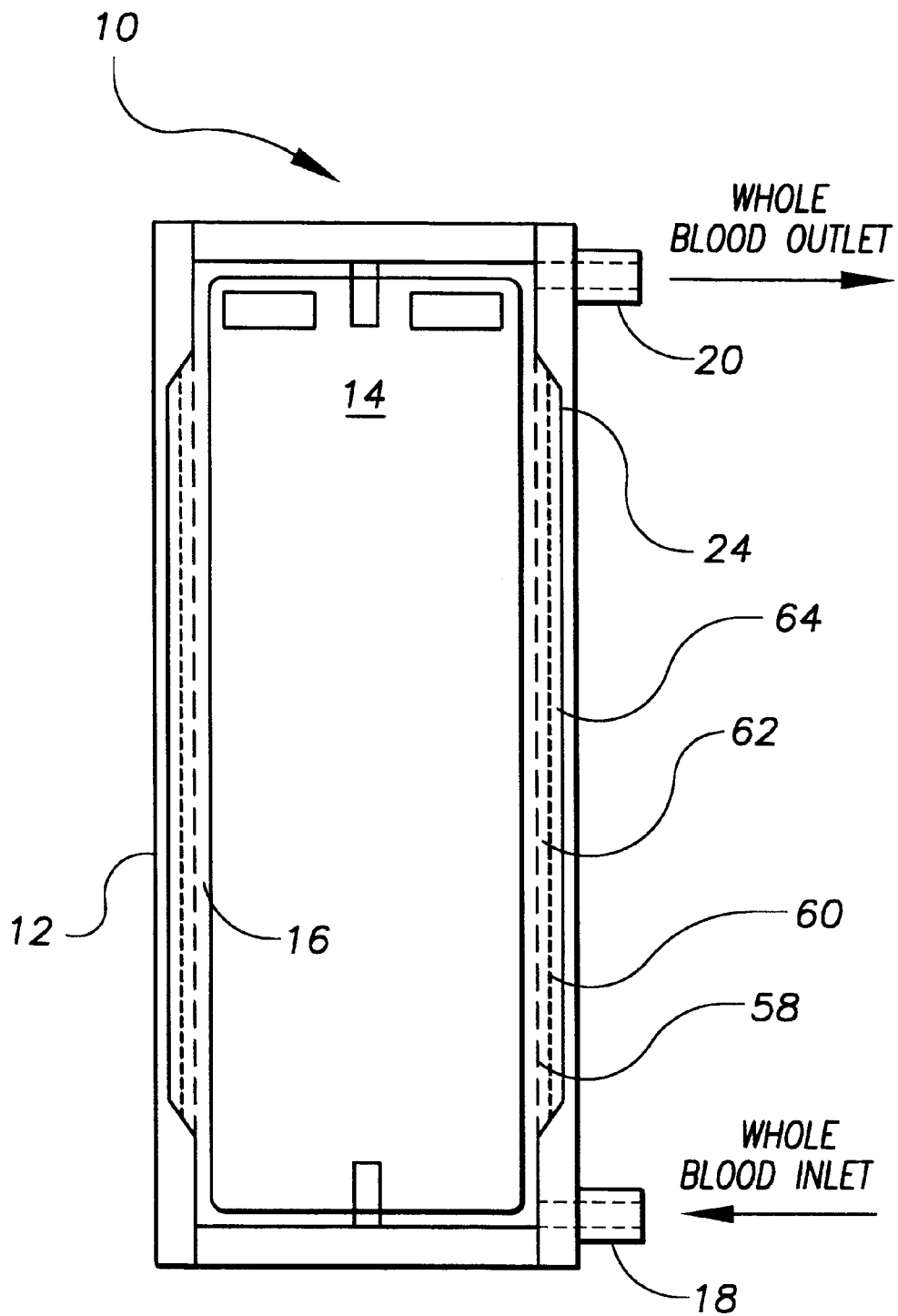
FIG. 4 is a cross sectional view of an embodiment of the invention being used for platelet collection.

Still another embodiment of the invention is shown in FIG. 4. In this embodiment, the reactor comprises two flexible permeable membranes 58 and 60. The first membrane 58 has a relatively large pore size on the order of 5 $\mu$m, while the second membrane has a smaller pore size on the order of less than about 2 $\mu$m. Thus, the first membrane will pass plasma and platelets, which have a size of about 2–4 $\mu$m, while the second membrane will pass only plasma. Main chamber 16 will then contain large blood components such as red and white blood cells, middle chamber 62 will contain platelets, and outermost chamber 64 will contain plasma. The vortex flow reactor and the undulations of the membranes ensure that plasma circulates quickly throughout the system and that clotting is minimized.

It should be noted that in the embodiments shown in FIGS. 1 and 2 the active species itself can be contained within the active compartments using a microporous membrane or an ultrafiltration membrane. The latter thus would eliminate the need to use a macroscopic polymeric support such as agarose. That is to say, by using an ultrafiltration membrane, heparinase itself could be contained in the active compartments without being immobilized on a substrate. In still other embodiments, multiple compartments of active materials may be provided, through which plasma passes either in series or in parallel. Alternatively, multiple immobilized active species may be provided within a single compartment.

In operation, (see FIG. 2) blood enters the apparatus 10 through a tangential bottom port 18 and flows upwardly through the annulus where blood plasma (which contains the substance to be modified or removed) is able to permeate the membranes and come into contact with the immobilized species while red cells, white cells and platelets are retained within the annulus 16. For direct control of the device output, an external pump can control the rate of plasma separation and contact time with the immobilized species thereby affecting the overall conversion. Plasma flow rate is directly related to the rotation rate of the inner cylinder 14 which creates the necessary shear rates to avoid membrane clogging and the physical properties of the membrane.

The apparatus 10 of FIGS. 1 and 2 can be employed to sufficiently remove drugs or toxins from whole blood if the appropriate immobilized species is used. An example is immobilized heparinase or urease for the removal of heparin or urea, respectively. Other immobilized species may bind to or break down materials such as $\beta_2M$ and various drugs which may be subject to overdose (e.g., tricyclic antidepressants).

Figure 5:
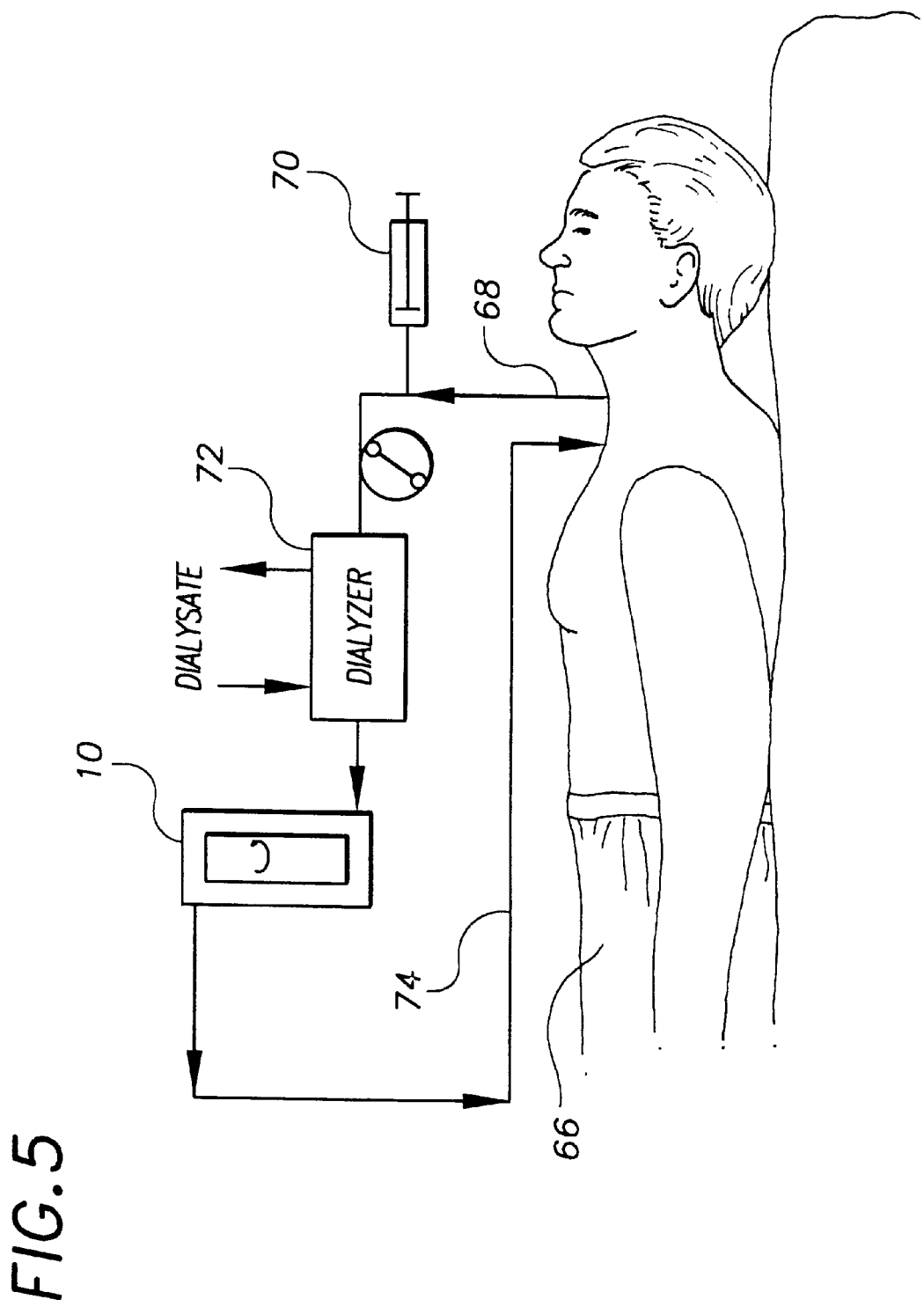
FIG. 5 is a schematic diagram illustrating the use of the bioreactor of the invention in a dialysis setting.

An immobilized heparinase will have a great impact in the treatment of acute renal insufficiency. FIG. 5 shows a patient 66 connected in a dialysis circuit. Blood from the patient 66 travels through a line 68 and is infused with heparin at 70. The heparinized blood is then pumped through dialyzer 72. The heparinized blood then travels into the vortex flow plasmapheretic reactor 10 of the invention.

The device 10 removes heparin by breaking it down and blood is then returned to the patient through the line 74. Anticoagulation is one of the most important components of renal replacement therapy and heparin is the oldest and most frequently used anticoagulant. In patients suffering from acute renal failure, the risk of bleeding is greatly increased and excessive anticoagulation may be the source of bleeding complications reported to occur in 5–26% of treatments. Current alternatives to systemic heparinization include variable heparin dosing, low molecular weight heparin, regional heparinization and neutralization with protamine, regional citrate anticoagulation with trisodium citrate, nefamostat mesilate, and prostaglandin analogue infusion. Despite these alternatives, acute kidney failure is a serious problem with unmet need for effective deheparinization.

The immobilized heparinase reactor of the invention is used in a regional heparinization regime and either of the two currently accepted methods to treat acute kidney failure: continuous renal replacement therapy (CRRT) and intermittent hemodialysis (IHD). In regional heparinization, heparin is infused into the circuit proximal to the dialyzer and the heparinase reactor located distal to the dialyzer degrades most of the heparin. With this configuration the patient has minimal exposure to heparin. The heparin degradation fragments have a much lower anticoagulant activity.

Preliminary in vitro tests of the reactor 10 of the invention with human blood have shown significant deheparinization and negligible blood damage. In addition, many experiments have been performed on live sheep. Results of these experiments are presented below in the Examples.

It is thus seen that the vortex flow plasmapheretic reactor of the invention efficiently removes drugs or toxins from whole blood when the appropriate immobilized species is used. The apparatus allows efficient and safe simultaneous separation and reaction within a compact device capable of handling whole blood. An important aspect of the invention is the circumparential flow in the active compartment via periodic membrane undulations. It is also important that there is no contact between blood cells and the immobilized species which will allow the use of the present apparatus in systems that employ proteins or enzymes that could damage the cell membrane such as phospholipase $A_2$. The system is compatible with whole blood which eliminates the need for separate external plasma separators which would involve extra costs and monitoring. Importantly, there is no net concentration of cells within the device and the device has the capability to lower the hematocrit of the blood only within the device to improve plasma flux through the membrane. The apparatus does not damage blood cells (hemolysis platelet aggregation), and there are no blood flow limitations. There is low priming volume (80 ml or lower), and the apparatus is easy to use in a clinical setting.

The apparatus of the invention can also be effectively used to remove toxins from blood without the use of an immobilized species via plasmapheresis as discussed above in conjunction with FIG. 3. In this embodiment, superior plasma fluxes (e.g. 50 ml/min) and longer operation times (up to 5 continuous hours without clogging) result from the design of the invention. This plasmapheresis technique is lower cost relative to the use of current systems which employ expensive hollow fiber filters or complicated and costly centrifugal devices. This aspect of the invention results in a significant improvement to the donation of plasma using the Baxter Autopherisis C unit due to the elimination of concentrated cell reinfusion cycles. This aspect cuts the donation time in half, lowers the anticoagulant dose needed to keep the system from clotting, and maintains a continuous process which allows for improved safety for the donor. The physical characteristics and fluid dynamics of the novel bioreactor design of the invention also have application in the research laboratory as an aid to carry out selective adsorption reaction processes with simultaneous separation of components. The mixing in the compartments helps minimize the processing time.

The bioreactor design of the invention is also applicable to nonbiological applications. For example, a series of compartments may be separated by membranes of successively reduced pore size as described above in conjunction with FIG. 4. Such a reactor can be used for efficient continuous size separation of solid particles in a slurry. As described above, the undulations of the membrane help keep the particles of the slurry fluidized, allowing the smallest particles to quickly pass through the membranes of successively reduced pore size to the final compartment. In another example, the reactor design may be used for catalysis of one or more components of mixtures or slurries. For example, a liquid phase may be separated from a solid phase as described above, and catalysts or reactants may be bound to solid supports for treatment of the liquid phase. This may be desirable, for example, in systems where the solid phase tends to poison the catalyst. Examples of suitable catalysis systems may be found in a number of chemistry texts, such as Crabtree, *The Organometallic Chemistry of the Transition Metals*, Wiley & Sons, 1988, particularly at Chapter 9.

EXAMPLES

Materials, Assays, and Methods

The equipment and methods used in the following examples were as follows: The reactor vessel was made from concentric polycarbonate cylinders (6.38 cm OD and 5.10 cm OD with 0.32 cm wall thickness) and sheets with polycarbonate inlet and outlet ports (0.357 cm ID). The gap between the inner cylinder and the membrane was 0.17 cm. The priming volume of the reactor was 45 ml, and the total reactor volume was 70 ml. The inner cylinder had a radius of 2.70 cm, and rotated on 0.32 cm OD stainless steel pins. Microporous polyester membranes (1 $\mu$m pore size) covered 11 cm of the 15 cm reactor length. Silicone O-rings were used to seal the inlet and outlet ports. Rotation of the inner cylinder was achieved via magnetic coupling of eight neodymium iron boron disc magnets (Dia=1.28 cm, Length=0.64 cm) and an external electric motor and controller. Rotation rate was detected through an optical sensor and displayed on a digital panel meter. Temperature measurements were made by T-type thermocouples connected to a digital panel meter.

Medical grade heparin for blood studies was porcine, 1,000 units/ml. Powdered heparin for enzyme activity determination was also porcine, 166 units/mg. Normal saline (0.9% NaCl) and PBS (0.154 M NaCl and 0.01 M sodium phosphate, pH=7.4) were used. Heparin levels in blood were monitored with Hemochron coagulation timers and glass activated test tubes.

Agarose particles were 6%, 100–200 mesh, 100 $\mu$m average diameter. Heparinase was produced from *Flavobac-*

*terium heparinum*. The enzyme preparation was 95% pure heparinase as determined by RP-HPLC (Company Documentation) with a specific activity of 242 IU/ml and a protein concentration of 2.6 mg/ml. One IU (international unit) is defined as the amount of enzyme required to produce 1 μmol of product per minute. Human blood was obtained from healthy male and female volunteers. Plasma hemoglobin levels were determined with an assay kit from Sigma Chemical Company (St. Louis, Mo.).

An assay using Azure 11 dye was used to monitor heparin concentrations during the experiments, according to the technique of Lam, "The separation of active and inactive forms of heparin," *Biochem. Biophys. Res. Commun.* 69:570–577, 1976, which is incorporated by reference herein. A 4.5 ml volume of the Azure II dye solution (0.01 mg/ml) was added to 0.5 ml of the heparin solution to be tested. The sample was mixed and incubated at room temperature for 1 minute before measuring the absorbance at 500 nm. A standard curve for this assay was prepared by using solutions of known heparin concentrations ranging from 0 to 3 USP units/ml heparin (~0–19 μg/ml). The standard curve was linear in the above range.

Whole blood recalcification times (WBRT) were used to indirectly determine the amount of heparin present in blood. Initially, a 200 μl volume of citrated blood (3.8% 1:10 dilution) was added to Hemochron ACT test tubes containing glass particles. Next, 200 μl of $CaCl_2$ was added to the test tube and the Hemochron 801 clot timer machine was immediately started. The test tube was gently mixed for 10 seconds and inserted into the test well of the Hemochron 801. The time required for a clot to form was recorded. The unknown samples were compared to a standard curve which was linear in the range of 0–4 USP units heparin/ml blood.

The Coomasie blue dye method of Bradford was used to measure the concentration of heparinase in buffered saline. A 800 μl sample was mixed with 200 μl of dye solution and incubated at room temperature for 5 minutes. The absorbance at 595 nm was measured and compared to a standard curve prepared with known bovine serum albumin concentrations ranging from 0 to 15 μg/ml. The standard curve was linear in this range.

The activity of heparinase I was defined using the international unit (IU). One IU is defined as the amount of heparinase that would produce 1 μmol of double bonds/min. The appearance of heparin degradation products was monitored at 232 nm in a quartz cuvette. Briefly, 20 gl of heparinase solution was added to 3 ml of heparin solution (2 mg/ml, in 100 mM MOPS and 5 mM calcium acetate pH 7.4) at 30° C. The initial rate was calculated from the slope of the curve and converted to IU using 3800 $M^{-1}$ molar absorptivity (1 cm path length).

One volume of agarose gel (100 μm average bead diameter) was washed with 10 volumes of deionized (DI) water to remove any preservatives. After resuspending the gel in 1 volume of DI water and 2 volumes of 2 M sodium carbonate, the suspension was chilled in an ice bath. Next, 0.15 volume of a cyanogen bromide in acetonitrile (1 g/ml) solution was added to the gel mixture, after which it was stirred vigorously in the fume hood for 5 minutes. Using a sintered glass funnel, the activated gel was isolated and washed with a mixture comprising 50 volume % DI water, 25 volume % I mM hydrochloric acid, and 25 volume % 0.1 M sodium bicarbonate 0.5 M NaCl pH 8.3 buffer.

After extensive washing of the activated gel, the heparinase solution (18 mg in 100 ml 0.1 M sodium bicarbonate 0.5 M NaCl pH 8.3) was incubated with the beads (100 ml) at 4° C. for 5 hrs to allow binding. Following heparinase binding, the immobilized heparinase was incubated overnight at 4° C. in a lysine solution (0.2 M lysine hydrochloride, 0.1 M sodium bicarbonate, and 0.5 M NaCl) to cap any unreacted sites. The immobilized heparinase was washed with a solution comprising 11 volume % cold pH 8.3 buffer and 67 volume % phosphate buffered saline (pH 7.4), and 22 volume % distilled water. The amount of bound protein was determined by a mass balance between the original enzyme solution and the washes.

The activity of the heparinase bound to the beads was measured using a modified UV 232 activity assay. A known volume of beads, approximately 0.1 ml, was added to 4 ml of a heparin solution (25 mg/ml). Under vigorous swirling at 37° C., 0.1 ml samples were taken at 1 minute intervals for 4 minutes and quenched in 0.9 ml of 30 mM HCl. The samples were centrifuged and the absorbance of the supernatant was measured at 232 nm. The activity was calculated from the slope between the data points using 5000 $M^{-1}$ as the molar absorptivity.

For the $β_2M$ studies, eleven murine, anti-$β_2M$ hybridoma cell lines have been produced following standard techniques, as summarized in Schlebusch, et al, "Production of a Single-Chain Fragment of the Murine Anti-Idiotypic Antibody ACA125 as Phage-Displayed and Soluble Antibody by Recombinant Phage Antibody Technique", *Hybridoma* 16(1):47–52, 1997, incorporated herein by reference. DNA polymerase chain reaction (PCR) was used to amplify the variable heavy ($V_H$) and variable light ($V_L$) sequences from hybridoma-derived complementary DNA. Through their ligation to a DNA strand encoding a polypeptide "linker", these $V_H$ and $V_L$ sequences were used to make single-chain antibody fragment (scFv) sequences, which were subsequently inserted into a plasmid vector. One scFv plasmid has been successfully expressed in *E. coli.* and qualitatively shown to bind $β_2M$ (Western blot). It will be apparent to those skilled in the art that these techniques can be used to generate a variety of scFvs specific for $β_2M$. Should it be found that the $β_2M$ in amyloid deposits is antigenically distinct from recombinant $β_2M$ (for example, due to end-stage glycation), antibodies may be produced using $β_2M$ obtained directly from clinical material (amyloid deposits). It is expected that 1–10 mg of such material will suffice to generate a second generation of monoclonal antibodies for scFv generation.

Example 1

Deheparinization in Saline

Regional heparinization studies were performed with the vortex flow plasmapheresis reactor (VFPR) of the invention. A 500 ml volume of the feed solution, heated to 32° C., was recirculated through the circuit at 120 ml/min with the plasma pump adjusted to 60 ml/min. The feed solution consisted of 100 mM MOPS and 5 mM $CaCl_2$ in isotonic saline adjusted to pH 7.4. The rotation rate of the inner cylinder was set to 1,200 rpm, which corresponds to a shear rate of 9,200 $s^{-1}$. This shear rate is below the hemolysis limit of 20,000 $s^{-1}$ reported in the literature (Heuser, et al., "A couette viscometer for short time shearing of blood," *Rheology,* 17:17–24, 1980; Fischel, et al., "Couette membrane filtration with constant shear stress," *Trans. Am. Soc. Artif Intern. Organs,* 34:375–385, 1988). Approximately 20 ml of immobilized heparinase (Specific activity 10–15 IU/ml wet gel) was injected into the active volume compartment of the VFPR and was fluidized by the flow dynamics in that chamber. The priming volume of the chamber was 45 ml. The infusion of heparin prereactor was adjusted to achieve clinically relevant heparin plasma concentrations which are in the range of 5–12 μg heparin/ml plasma.

Heparin concentrations were measured at the inlet and outlet of the reactor using the Azure II assay.

Figure 6:
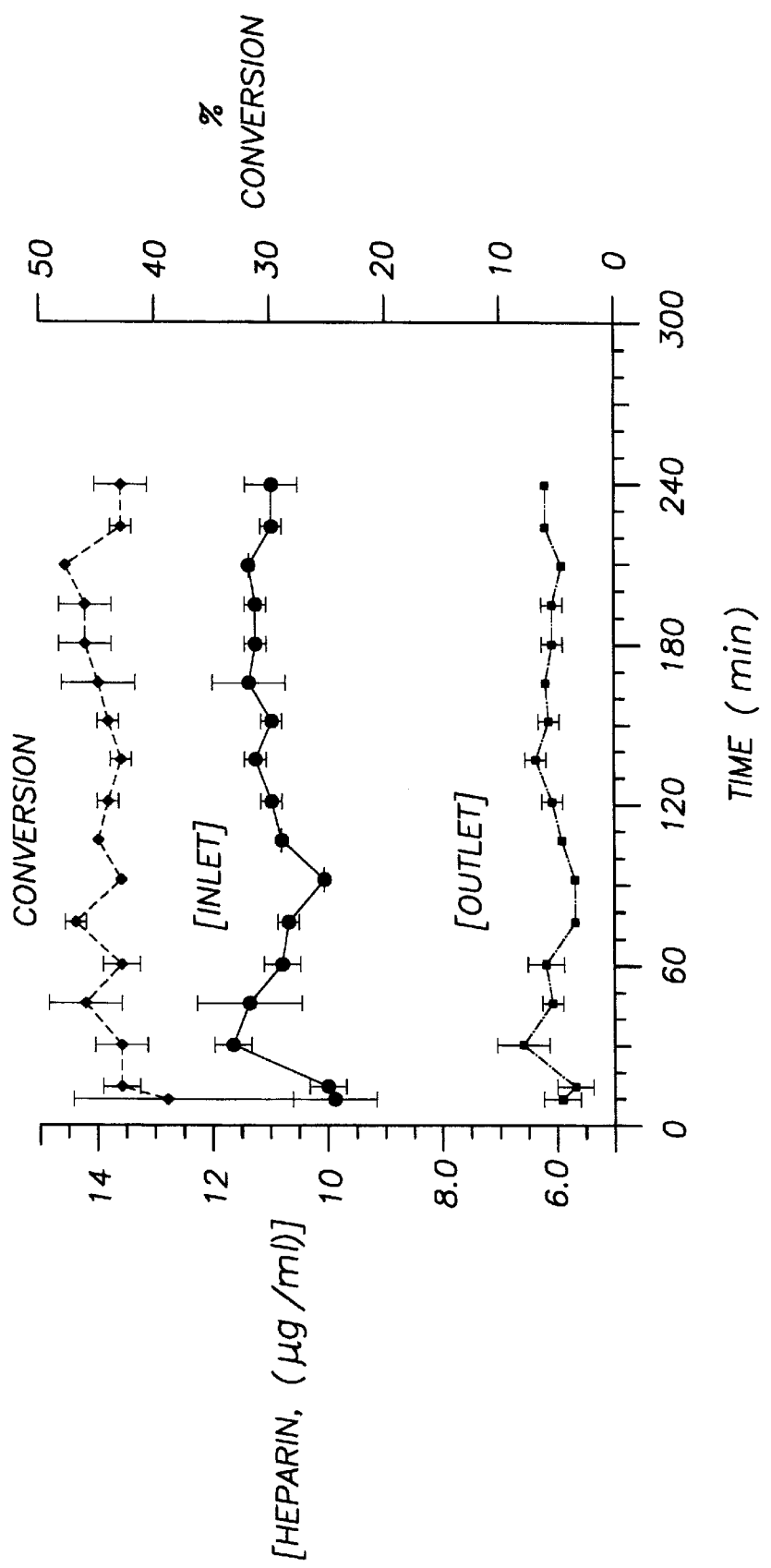
FIG. 6 is a graph of the performance of the vortex flow plasmapheresis reactor of Example 1 in saline.

As discussed earlier, the VFPR design was intended to overcome the "blood compatibility" and throughput issues associated with agarose immobilized heparinase I. The results of the VFPR experiments in saline are shown in FIG. 6. The reactor maintained mean inlet and outlet heparin concentrations of 11±0.5 and 6.0±0.2 μg/ml (±S.E.M.), respectively. These values corresponded to a mean heparin conversion of 44±0.5% (±S.E.M.) for an inlet flow rate into the reactor of 120 ml/min and a plasma pump flow rate of 60 ml/min. This heparin conversion, if achieved in a patient, would meet the minimum efficacy design criteria for an immobilized heparinase reactor as stated in the introduction. It is expected that the overall heparin conversion through the device would depend on the amount of immobilized enzyme, the fluidization conditions, and the flow split through the microporous membrane.

Example 2
Deheparinization in Sheep

Figure 7:
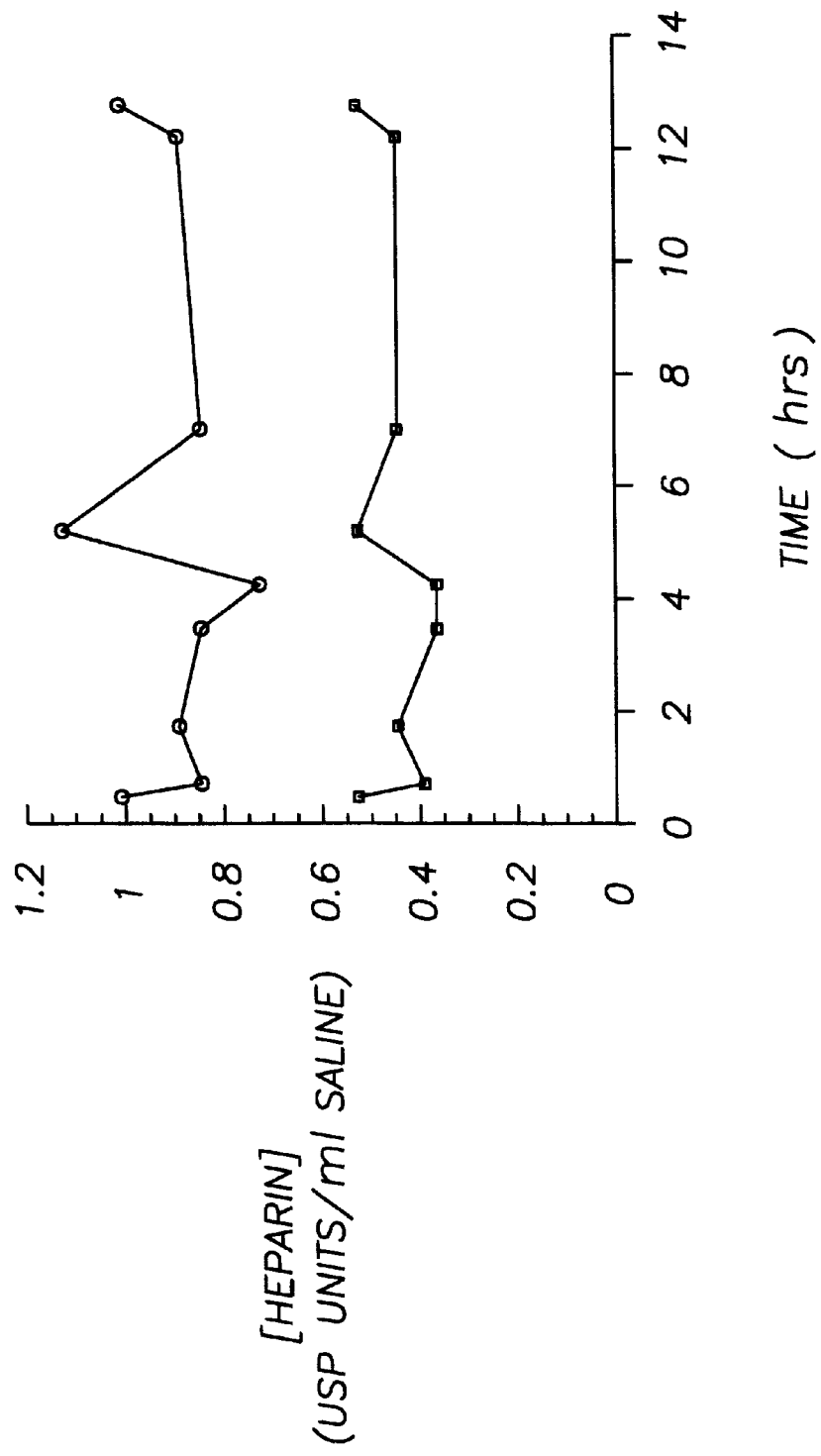
FIG. 7 is a graph of heparin versus time at the reactor inlet and reactor outlet in the live sheep experiment of Example 2.
Figure 8:
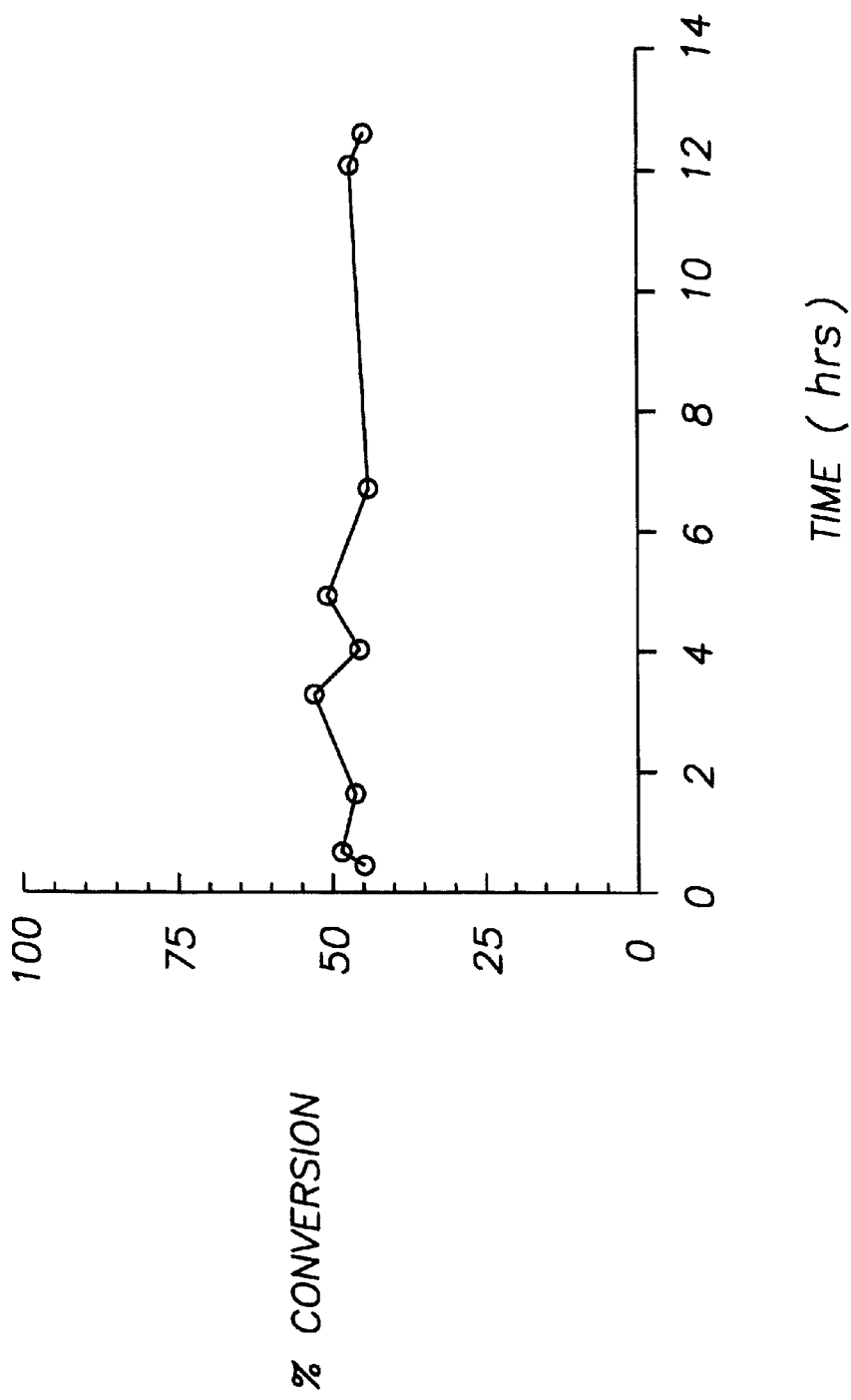
FIG. 8 is a graph showing the percent conversion versus time for a single pass conversion in saline in the live sheep experiment of Example 2.
Figure 9:
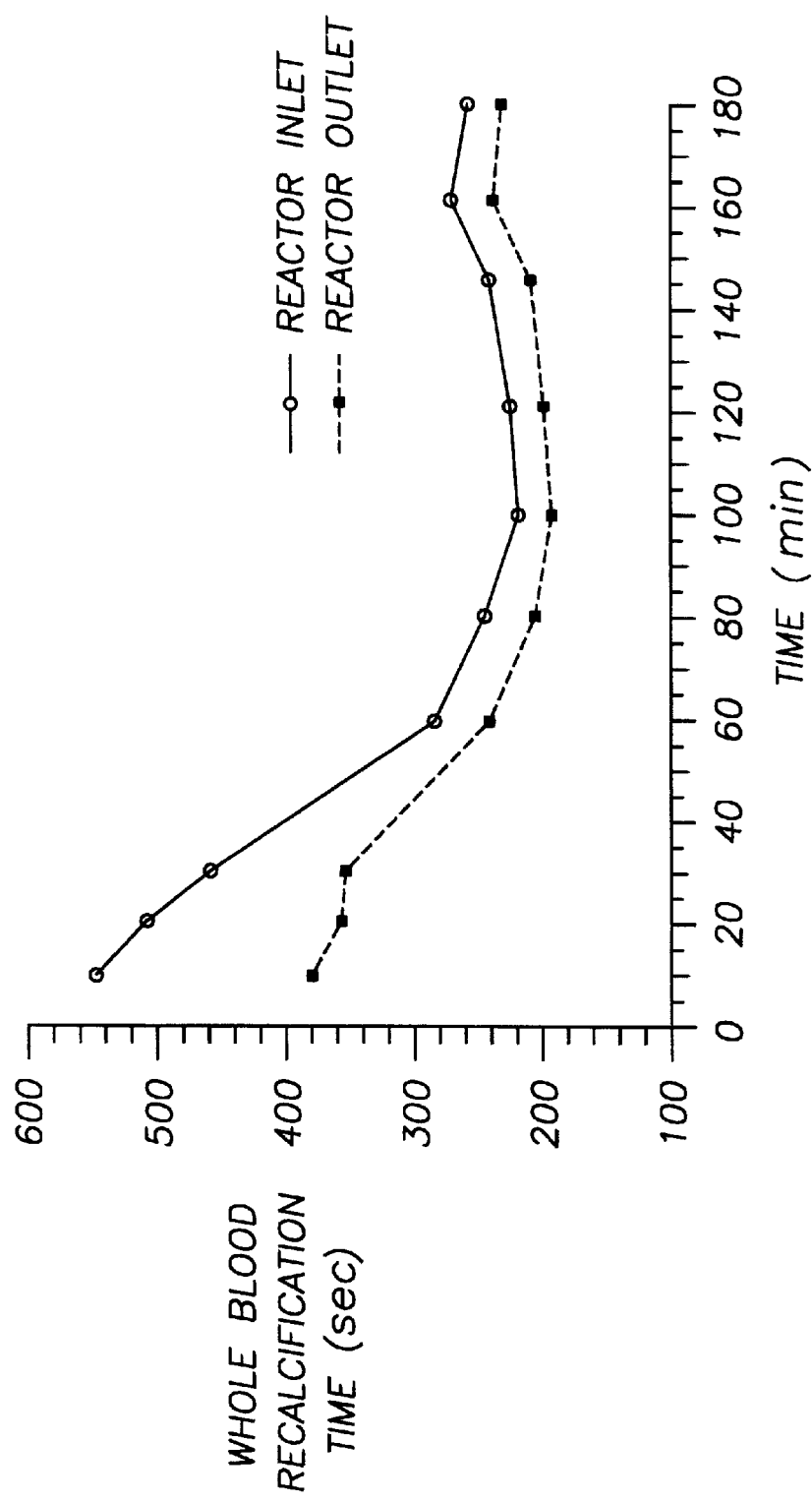
FIG. 9 is a graph of whole blood recalcification time versus time for a inlet and outlet whole blood recalcification times for immobilized heparinase reactor in the live sheep experiment of Example 2.
Figure 10:
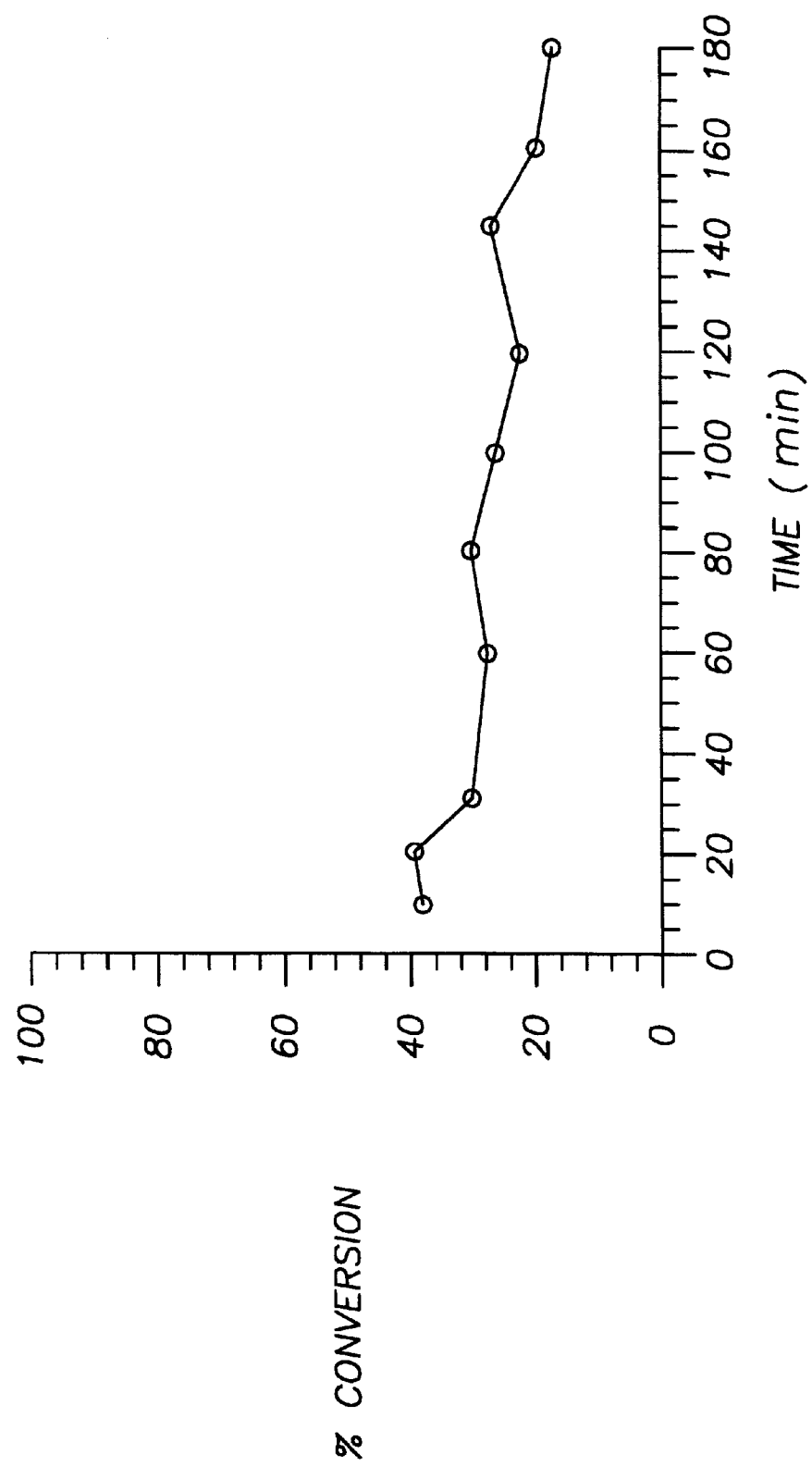
FIG. 10 is a graph of percent conversion versus time for immobilized heparinase reactor in the live sheep experiment of Example 2.
Figure 11:
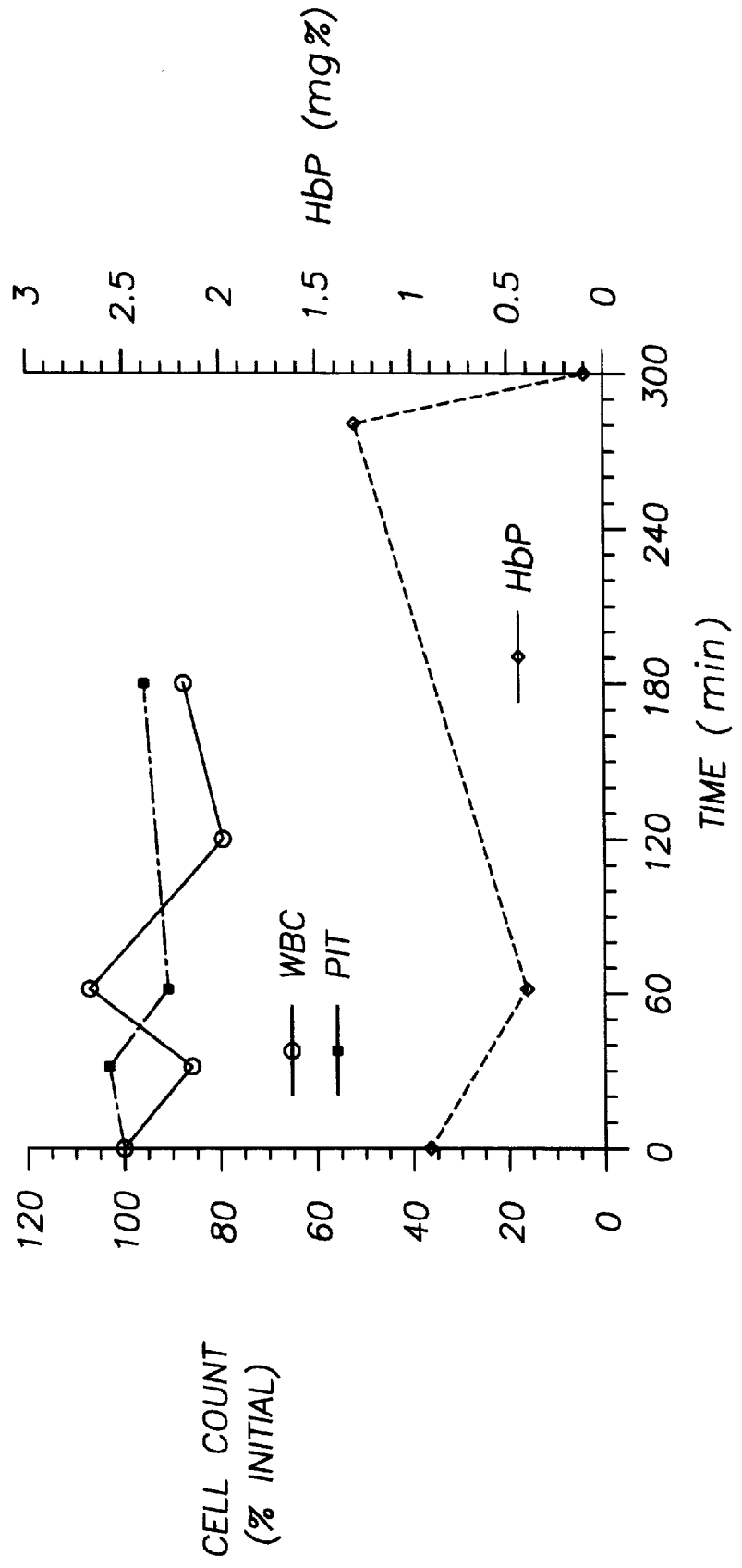
FIG. 11 is a graph of cell count versus time illustrating reactor blood compatibility data for sheep.
Figure 12:
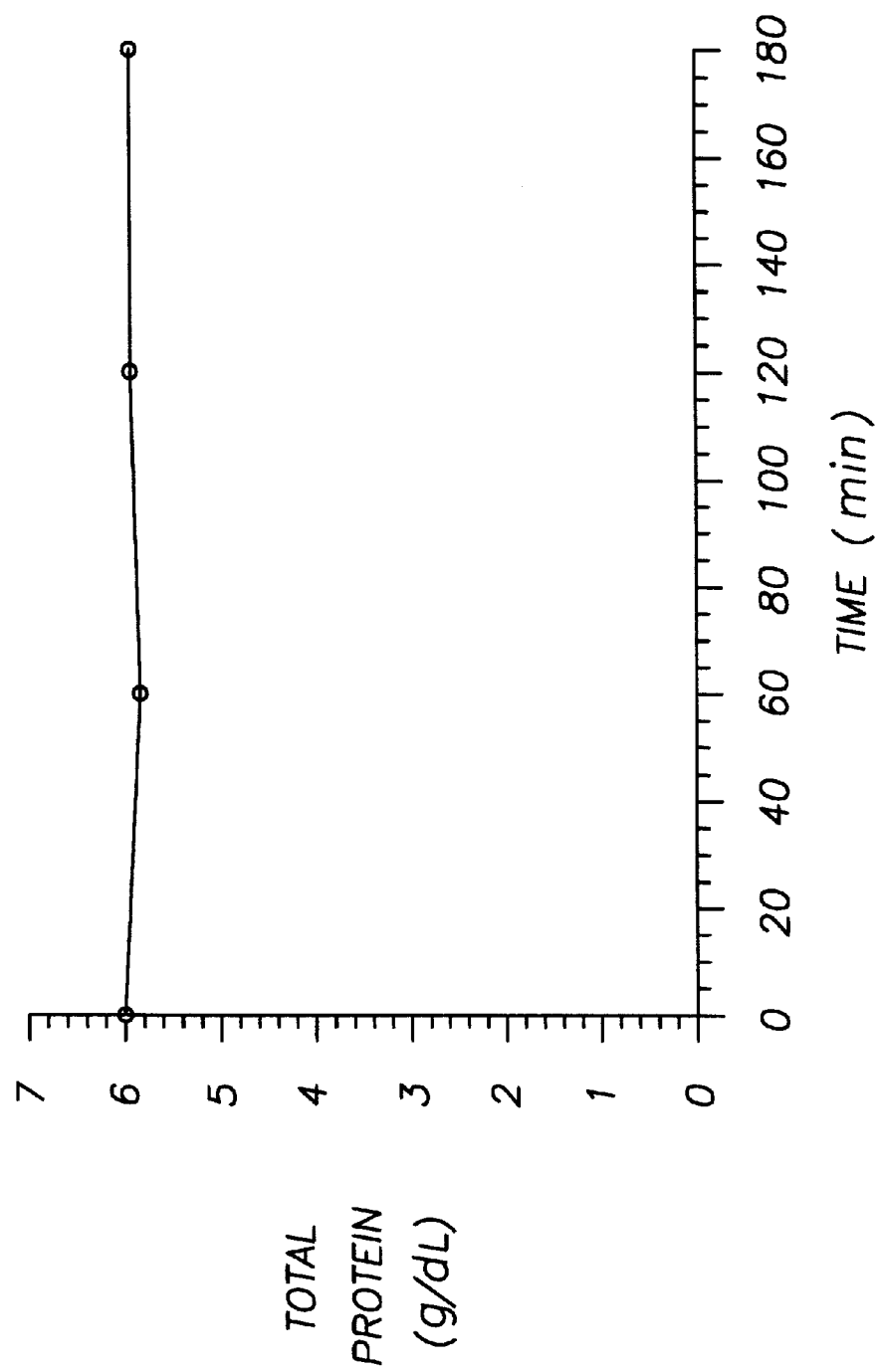
FIG. 12 is a graph of total protein versus time during an excorporeal procedure with the immobilized heparinase reactor in the live sheep experiment of Example 2.
Figure 13:
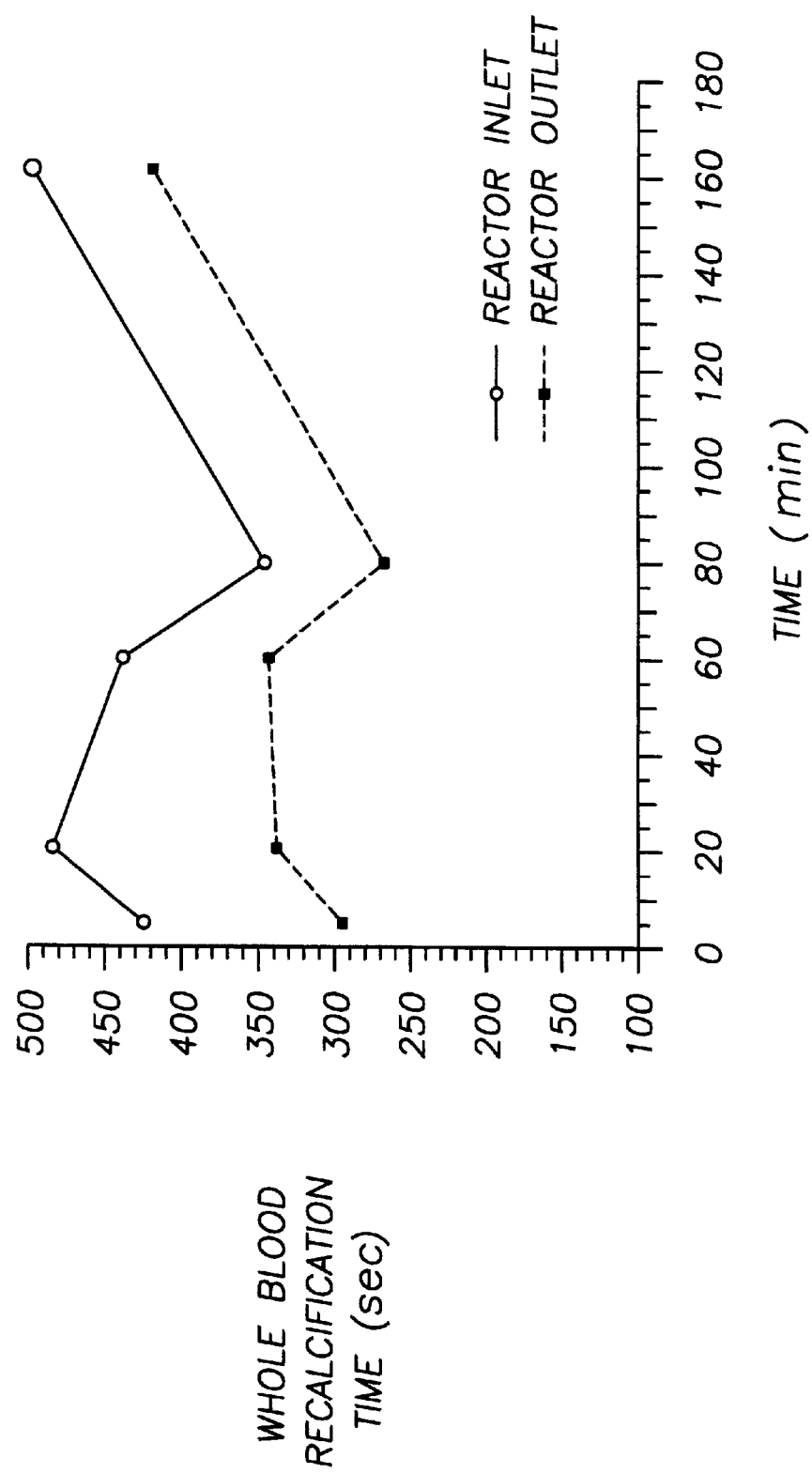
FIG. 13 is a graph of whole blood recalcification time versus time for inlet and outlet heparin levels for immobilized heparinase reactor in the live sheep experiment of Example 2.
Figure 14:
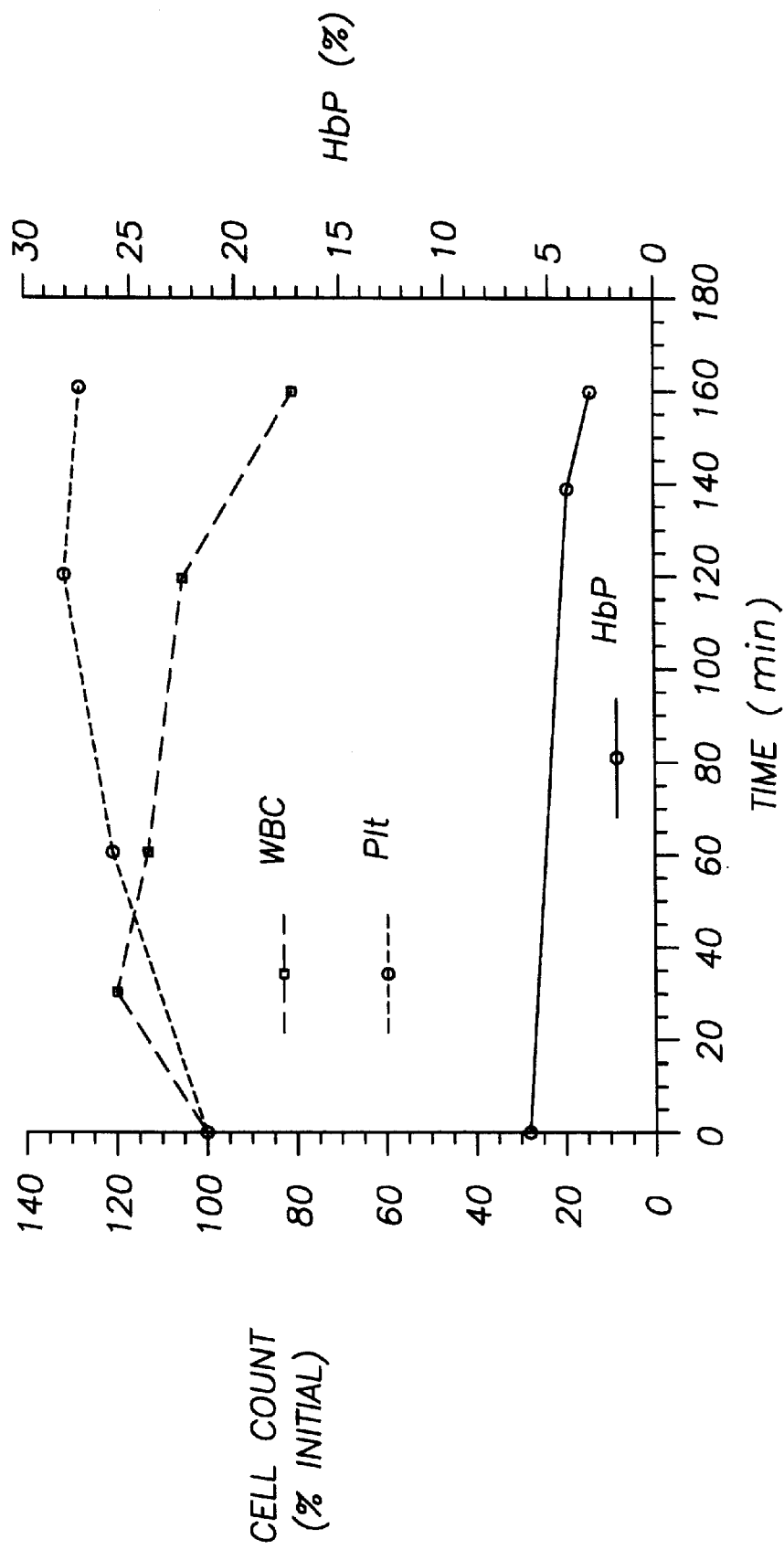
FIG. 14 is a graph of cell count versus time illustrating reactor blood compatibility data for sheep.
Figure 15:
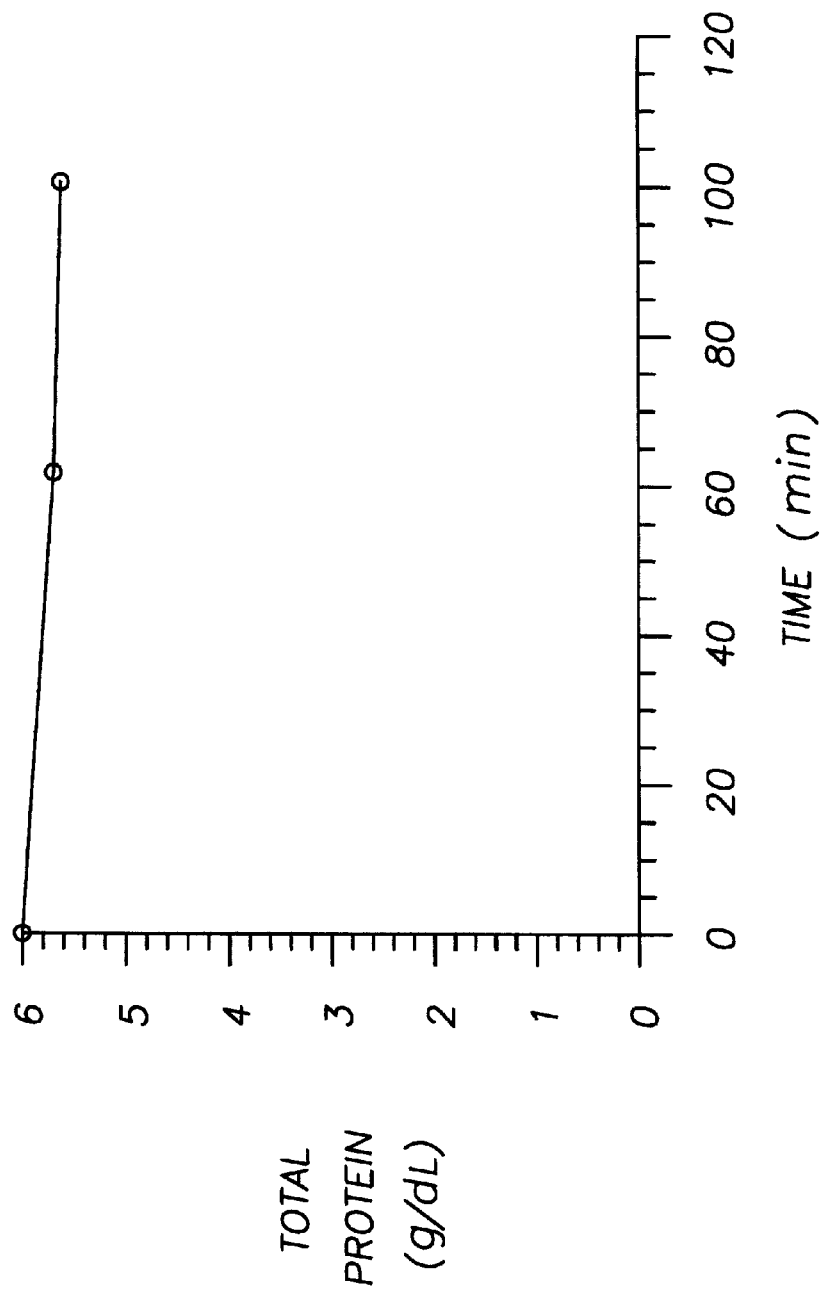
FIG. 15 is a graph of total protein versus time in a sheep experiment.
Figure 16:
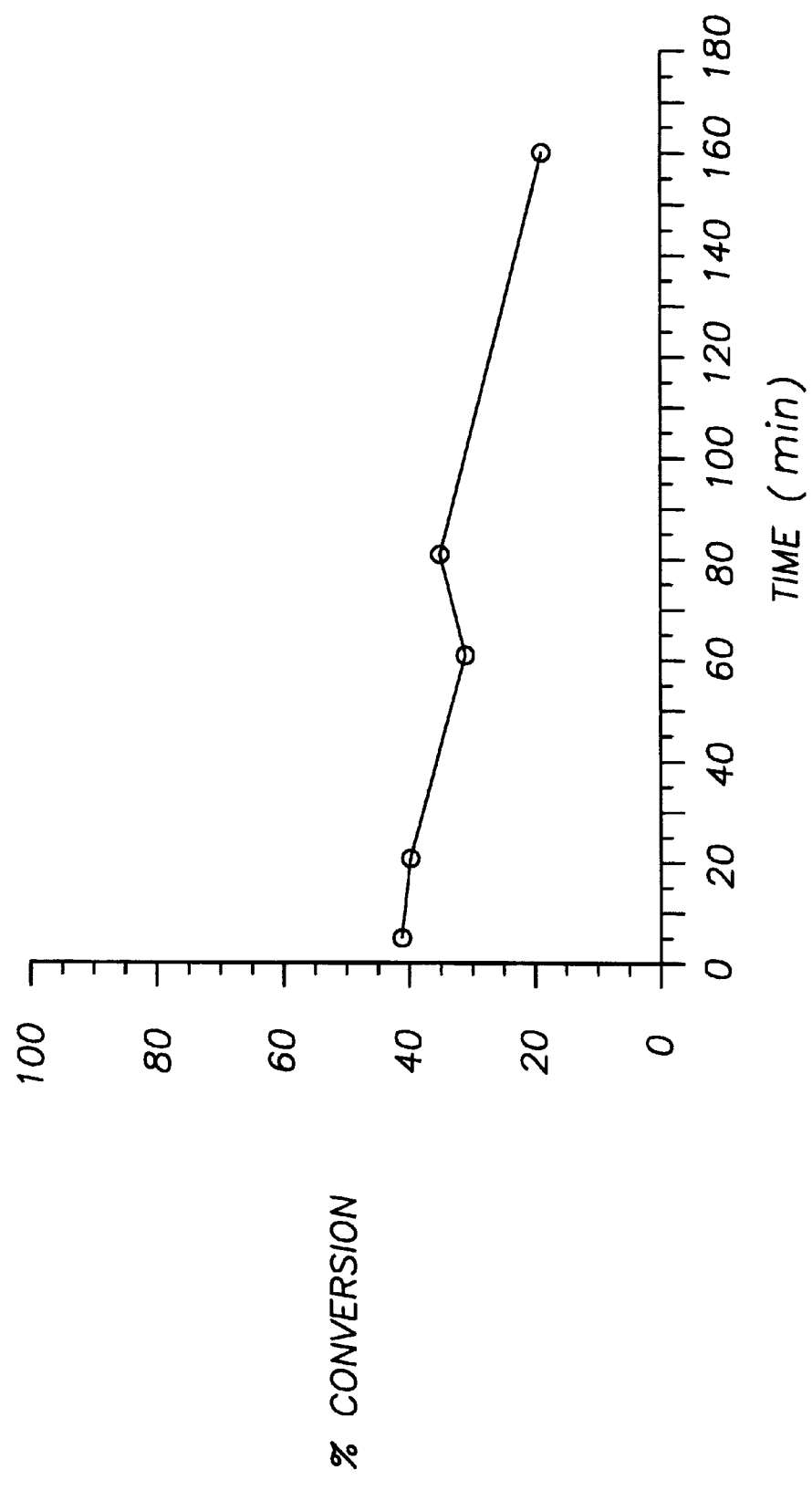
FIG. 16 is a graph of percent conversion versus time in an experiment with sheep.

The bioreactor configuration of FIG. 1 was tested in live sheep, and the results are presented in FIGS. 7–17. In FIG. 7 heparin concentrations at the reactor inlet are shown by the circles and at the outlet by squares. The flow rate was 120 milliliters per minute which is equivalent to 200 milliliters per minute whole blood assuming a hematocrit of 40. The temperature of the experiment was 33° C. FIG. 8 shows reactor conversion in saline and a flow rate of 120 milliliters per minute (200 milliliters per minute whole blood assuming a hematocrit of 40). The temperature of this experiment was 33° C. FIG. 9 shows inlet and outlet whole blood recalcification times for the immobilized heparinase reactor. Blood flow rate was 150 millimeter per minute and base line WBRT was 115 seconds. Reactor temperature was 36° C. FIG. 10 shows conversion for immobilized heparinase reactor at a blood flow rate of 150 milliliter per minute. The theoretical target conversion was 40%. FIG. 11 shows reactor blood compatibility data for sheep. FIG. 12 illustrates total protein during extracorporeal procedure with immobilized heparinase reactor. FIG. 13 shows inlet and outlet heparin levels for immobilized heparinase reactor in another sheep experiment. Blood flow rate was 150 milliliters per minute and base line WBRT was 115 seconds. FIG. 14 illustrates reactor blood compatibility data for sheep. FIG. 15 is a graph showing total protein during the extra corporeal procedure with immobilized heparinase reactor. FIG. 16 shows reactor conversion with time. Blood flow rate was 150 milliliters per minute.

Figure 17:
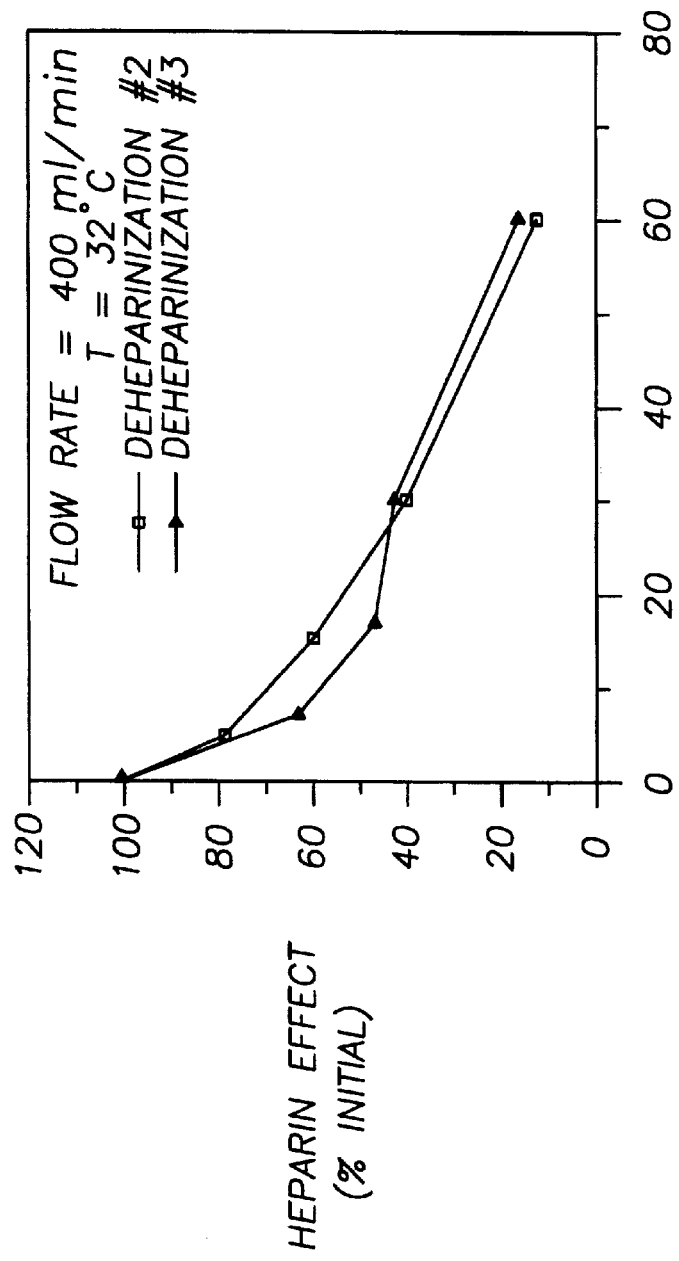
FIG. 17 is a graph of heparin effect versus time in a membrane reactor using sheep blood.

FIG. 17 shows heparin effect as a function of time. The base line whole blood recalcification time (WBRT) of the donor was 112 seconds. The circuit was heparinized to an initial WBRT of 341 seconds and the reactor reduced it to a final WBRT of 140 seconds. For deheparinizations number 2 and number 3, the circuit was reheparinized from 140 seconds to 340 and 350 seconds, respectively. The final WBRT for deheparinization number 2 and number 3 were 140 and 150 seconds, respectively. The data are an average of four measurements on a Hemochron 801 clotting time tester (International Technidyne Corporation).

Example 3
Deheparinization of Human Whole Blood

The assembled reactor was incorporated into a closed circuit primed with normal saline. The circuit consisted of a blood warmer, blood pump, drip chamber and pressure monitor. The experimental set up was similar to the VFPR saline studies. A 450 cc volume of human donor blood was collected in heparin at the Blood Donor Center of Children's Hospital of Boston. The hematocrit (% of blood cells) of the bag was adjusted to 30–35% by dilution with saline to match the values normally encountered in the clinical setting. The blood was pumped at a flow rate of 160 ml/min. The VFPR rotation rate was set at 1,200 rpm and the plasma pump was set at 60 ml/min. The temperature of the blood circuit was constant at 33° C. A pressure gauge was placed between the active volume compartment outlet and the plasma pump to monitor clogging of the microporous membrane. Blood samples were taken at the inlet and outlet of the device and heparin levels were indirectly assayed by WBRT's. Blood samples also were drawn at the reactor outlet for further hemocompatibility tests.

Figure 18:
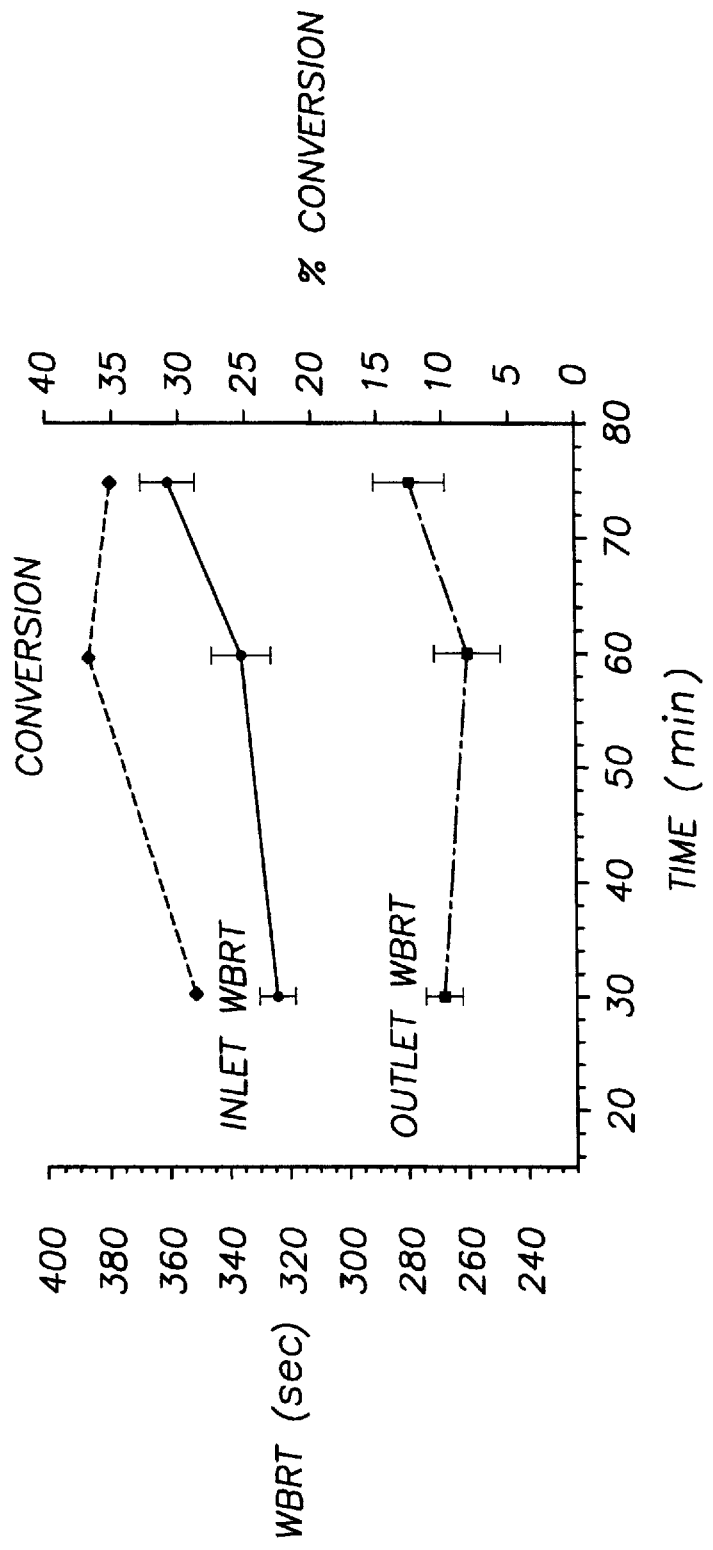
FIG. 18 is a graph of the performance of the vortex flow plasmapheresis reactor of Example 3 with human blood in vitro.

Even though good heparin neutralization results were obtained in the saline experiments of Example 1 and the sheep experiments of Example 2, the important measure for an immobilized heparinase reactor is its performance in human blood. The results for regional blood heparinization using 10 ml of agarose immobilized heparinase (specific activity 16 IU/ml gel) are shown in FIG. 18. The reactor maintained a mean WBRT difference of 67 seconds between the inlet and outlet. This difference corresponded to a mean heparin conversion of 34±2% (±S.E.M.) at a blood flow rate of 160 ml/min and a plasma pump flow rate of 60 ml/min.

Blood was tested before and after the deheparinization experiment to determine whether the treatment caused any blood damage. It was found that white and red cell counts changed by less than 3% of their initial values. The platelet count had an 8% reduction relative to the concentrations at the beginning of the run. The concentrations of free hemoglobin released into the plasma were well below the safety criteria of 150 mg/dL. Therefore, eliminating contact between the cells and the agarose beads was an efficient way to significantly reduce hemolysis. These results are favorable when compared to those of previous immobilized heparinase reactors in which fluidized agarose beads within whole blood negatively affected the cell counts (e.g., Larsen, et al., "Effect of extracorporeal enzymatic deheparinization on formed blood components," *Artif Organs,* 8(2):198–203, 1984).

It is important to know whether an extracorporeal device is nonspecifically depleting proteins in blood. This is especially important for an immobilized heparinase reactor because the anticoagulant activity of heparin in blood depends on the presence of many other proteins in the "clotting cascade", specifically antithrombin III. Relative changes in total serum protein, antithrombin III, and fibrinogen for a reactor run were measured to assess this aspect of reactor performance. Total protein (primarily albumin and immunoglobulins) and antithrombin values were unchanged during the experimental run. Fibrinogen, a precursor protein to fibrin clots and a measure of the degree of fibrin generation within the system, dropped 13% over the course of the 60 minute run. Nevertheless, there were no fibrin clots visible to the naked eye upon inspection of the device after the experimental run. This observation does not rule out the possibility that microclots may be forming on the surface of the beads. However, the VFPR was considered to have fulfilled the safety design criteria regarding device effect on blood cells and platelet count.

Example 4
Removal of $\beta_2 M$ From Blood

A preliminary study of the removal of $\beta_2 M$ using the bioreactor of the invention has been carried out. The scFvs used in the study have several advantages, including reduced cost, smaller size (and therefore higher achievable density), and relatively easy surface immobilization.

The scFvs are bound with a polypeptide linker that can be engineered to bind to a variety of supports. For example, any primary amine (lysine side chain) can be biotinylated using the biotin derivative, biotin N hydroxysuccinimide ester. The biotinylated polypeptide or antibody can then be conjugated to any solid support with an accessible avidin or streptavidin molecule. For example, streptavidin coated agarose beads are commercially available (Promega, Madison, Wis.) and can be used as a solid support for the scFvs. As will be apparent to those skilled in the art, many other binding systems are possible and the exact characteristics of the linker and the binding system are not intended to limit the invention. As another specific example, the scFvs could be bound to liposomes by alkylation/esterification with fatty acid derivatives, as described in DeKruif, et al., "Biosynthetically lipid-modified human scFv from phage libraries as targeting molecules for immunoliposomes," *FEBS Lett.* 399:232–236, 1996, incorporated herein by reference. It may be desirable to use hydrophilic supports in order to promote dispersion of the supports in the plasma.

The scFvs have the further advantage that site-directed or random mutagenesis can be used to further boost $\beta_2M$ affinities by as much as one or two orders of magnitude, to a binding affinity on the order of $10^8$ or more. See, for example, Schier, et al., "Isolation of picomolar affinity anti-c-erbB-2 single chain Fv molecular evolution of the complementarity determining regions in the center of the antibody binding site," *J Mol. Biol.* 17:551–567, 1996, incorporated herein by reference. The scFvs may, for example, be engineered to contain an unpared thiol close to or at the $COOH^-$ terminus of the scFv, by introduction of a cysteine residue. This mutation may facilitate binding of the scFv by a strepavidin-based approach, for example.

This study assessed the feasibility of immobilized antibodies to adsorb $\beta_2M$ from solution and approximated the capacity of such a system. From the measured data an estimation of the reactor size required to clear 0.2 gm of $\beta_2M$ was formulated. Commercially available, intact anti-$\beta_2M$ antibodies (BBM.s; 150 k Da) were bound to Protein A beads in an oriented fashion, with the $\beta_2M$ binding sites exposed. An average of 0.05 $\mu$M of BBM.1 bound per ml of beads. Studies were conducted in 1 ml columns, where it was found that in saline containing 60 $\mu$g/ml of $\beta_2M$ about 0.04 $\mu$M of $\beta_2M$ per ml of beads was removed in one hour, suggesting an approximate antibody-antigen binding ratio of 1:0.8. Extrapolating these data to scFv (27 k Da), and assuming the same binding ratio and affinity and a 40% bead volume in the reactor, 0.2 g of $\beta_2M$ can be removed by a 350 ml active volume. In a typical dialysis session, the reactor should remove at least 0.2 g (the circulating concentration of $\beta_2M$) in order to halt $\beta_2M$ accumulation, and possibly 0.5 g or more in order to restore elevated $\beta_2M$ levels to normal.

This represents a maximum reactor volume, however. The VFPR described above has much higher mass transfer rates than a packed column, and it is therefore expected that much smaller active volumes can be achieved. Improvement of the binding affinity of the scFvs by mutagenesis as described above is expected to further reduce the necessary reactor volume, and it is believed that active volumes of 50 ml or less are readily achievable while meeting target $\beta_2M$ removal levels.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. Apparatus for removing a substance from whole blood comprising:
    concentric outer and inner cylinders defining an annulus therebetween, the inner cylinder adapted for rotation with respect to the outer cylinder;
    at least one of an inner surface of the outer cylinder or an outer surface of the inner cylinder including a porous membrane covered portion forming a compartment containing an immobilized species, the species adapted to remove the substance;
    an inlet for introducing blood into the annulus for flow along the cylinders; and
    an outlet port for discharging the blood,
    wherein the porous membrane allows plasma within the blood to interact with the immobilized species while restricting blood cells from interacting with the immobilized species.

2. The apparatus of claim 1 wherein the rotation of the inner cylinder generates Taylor vortices in the annulus, the vortices creating oscillating pressure gradients within the annulus, the pressure gradients causing periodic undulations in the porous membrane resulting in circumferential flow in the compartment containing the immobilized species.

3. The apparatus of claim 1 or 2 wherein both inner and outer cylinders have membrane covered portions containing immobilized species.

4. The apparatus of claim 1 or 2 wherein the inner surface of the outer cylinder includes a recess covered by a mesh to exclude the immobilized species, the recess acting as a collection chamber for plasma after interaction with the immobilized species.

5. The apparatus of claim 4 further including a pump for circulating plasma from the recess into the annulus.

6. The apparatus of claim 1 or 2 wherein the species is immobilized on agarose beads.

7. The apparatus of claim 6 wherein the substance is heparin and the immobilized species is heparinase.

8. The apparatus of claim 1 or 2 wherein the substance is $\beta_2M$-microglobulin and the immobilized species comprises single chain antibody fragments.

9. The apparatus of claim 8 wherein the apparatus is adapted to remove at least 0.2 g $\beta_2M$-microglobulin in a period of less than about three hours.

10. The apparatus of claim 8 wherein the apparatus is adapted to remove at least 0.5 g $\beta_2M$-microglobulin in a period of less than about two hours.

11. The apparatus of claim 8 wherein the apparatus has an active volume of less than about 350 ml.

12. The apparatus of claim 8 wherein the apparatus has an active volume of less than about 200 ml.

13. The apparatus of claim 8 wherein the apparatus has an active volume of less than about 50 ml.

14. The apparatus of claim 1 or 2 wherein the apparatus has a transmembrane flow rate of greater than about 50 ml/min.

15. The apparatus of claim 1 or 2 wherein the apparatus has a transmembrane flow rate of greater than about 100 ml/min.

16. The apparatus of claim 1 or 2 wherein the apparatus has a transmembrane flow rate of greater than about 200 ml/min.

17. The apparatus of claim 2 wherein the immobilized species is immobilized on beads, and wherein the beads are fluidized by the circumferential flow in the compartment.

18. The apparatus of claim 17 wherein the beads comprise a material selected from the group consisting of agarose, cellulose, and protein A.

19. The apparatus of claim 1 or 2 wherein the active species is in the form of micelles.

20. The apparatus of claim 1 or 2 wherein the inner cylinder rotates via magnetic coupling to an external motor.

21. The apparatus of claim 12 wherein the inner cylinder rotates at approximately 1200 r.p.m.

22. The apparatus of claim 1 or 2 wherein the active species is selected from the group consisting of antibodies, antibody fragments, catalytic antibodies, enzymes, peptides, proteins, or living cells.

23. Apparatus for collecting platelets from blood comprising:

concentric outer and inner cylinders defining an annulus therebetween, the inner cylinder adapted for rotation with respect to the outer cylinder;

at least one of an inner surface of the outer cylinder or an outer surface of the inner cylinder including two parallel porous membranes defining a first compartment therebetween and a second compartment between the membranes and the surface, the membrane closest to the surface having a pore size adapted to restrict the passage of platelets and the membrane farthest from the surface having a pore size adapted to allow the passage of platelets but to restrict the passage of other blood components;

an inlet for introducing blood into the annulus for flow along the cylinders;

means for removing platelets from the first compartment; and an outlet port for discharging the blood.

24. An apparatus for continuous treatment of a mixture comprising liquid and solid components, comprising:

concentric outer and inner cylinders defining an annulus therebetween, the inner cylinder adapted for rotation with respect to the outer cylinder;

at least one of an inner surface of the outer cylinder or an outer surface of the inner cylinder including a porous membrane covered portion forming a compartment containing a reactant for treatment of the liquid component of the mixture;

an inlet for introducing the mixture into the annulus for flow along the cylinders; and an outlet port for discharging the mixture, wherein the porous membrane allows the liquid portion of the mixture to interact with the reactant while restricting the solid portion of the mixture from interacting with the reactant.

* * * * *